(12) United States Patent
Bibian et al.

(10) Patent No.: US 10,130,766 B1
(45) Date of Patent: Nov. 20, 2018

(54) INTELLIGENT PHARMACEUTICAL DELIVERY SYSTEM WITH AUTOMATIC SHUTOFF AND METHOD OF USING

(71) Applicants: Stéphane Bibian, Cleveland Heights, OH (US); Tatjana Zikov, Cleveland Heights, OH (US)

(72) Inventors: Stéphane Bibian, Cleveland Heights, OH (US); Tatjana Zikov, Cleveland Heights, OH (US)

(73) Assignee: NeuroWave Systems Inc., Cleveland Heights, OH (US)

( * ) Notice: Subject to any disclaimer, the term of this patent is extended or adjusted under 35 U.S.C. 154(b) by 420 days.

(21) Appl. No.: 14/874,736

(22) Filed: Oct. 5, 2015

Related U.S. Application Data

(63) Continuation-in-part of application No. 13/962,565, filed on Aug. 8, 2013.

(60) Provisional application No. 61/680,888, filed on Aug. 8, 2012.

(51) Int. Cl.
| | | |
|---|---|---|
| *A61M 21/00* | (2006.01) | |
| *A61M 5/172* | (2006.01) | |
| *A61B 5/0476* | (2006.01) | |
| *A61B 5/00* | (2006.01) | |
| *A61B 5/04* | (2006.01) | |
| *A61M 16/00* | (2006.01) | |

(52) U.S. Cl.
CPC ....... *A61M 5/1723* (2013.01); *A61B 5/04012* (2013.01); *A61B 5/0476* (2013.01); *A61B 5/4821* (2013.01); *A61B 5/4839* (2013.01); *A61M 16/0003* (2014.02); *A61M 2202/048* (2013.01); *A61M 2205/18* (2013.01); *A61M 2230/005* (2013.01); *A61M 2230/10* (2013.01)

(58) Field of Classification Search
CPC .... A61M 21/00; A61M 19/00; A61M 5/1723; A61M 2005/1405; A61M 2005/14208; A61M 2005/14296; A61M 2205/6036; A61M 2205/6045; A61M 2205/6054; A61M 2205/6063; A61M 2205/6072; A61M 2205/6081; A61M 2205/609; A61B 5/0476; A61B 5/0478; A61B 5/048; A61B 5/4821; G06F 19/3468
See application file for complete search history.

(56) References Cited

U.S. PATENT DOCUMENTS

| | | | | |
|---|---|---|---|---|
| 5,906,208 | A | * 5/1999 | Ishikawa | ............ A61B 5/04002 128/200.24 |
| 2004/0079372 | A1 | * 4/2004 | John | .................... A61B 5/048 128/204.18 |

(Continued)

*Primary Examiner* — Bhisma Mehta
*Assistant Examiner* — William Frehe
(74) *Attorney, Agent, or Firm* — Brian Kolkowski

(57) ABSTRACT

A system and method provides closed-loop sedation, anesthesia, or analgesia by monitoring EEG and automatically adjusting the delivery of sedative, anesthetic, and/or analgesic drugs to maintain that desired or predetermined level of cortical at all echelons of care. The system and method further monitor the subject's cortical activity to detect occurrence of burst suppression which can be indicative of unsafe depth of anesthesia or sedation. Further, the system and methods provide for alteration or cessation of the administration of anesthesia or sedation based on the occurrence of burst suppression to mitigate harm to the subject.

20 Claims, 29 Drawing Sheets

(56) References Cited

U.S. PATENT DOCUMENTS

2006/0047538 A1* 3/2006 Condurso ............. G06F 19/326
                                                       705/3
2009/0275892 A1* 11/2009 Molnar ................ A61B 8/4218
                                                     604/116
2011/0295196 A1* 12/2011 Chazot ................ A61M 5/1723
                                                      604/66

\* cited by examiner

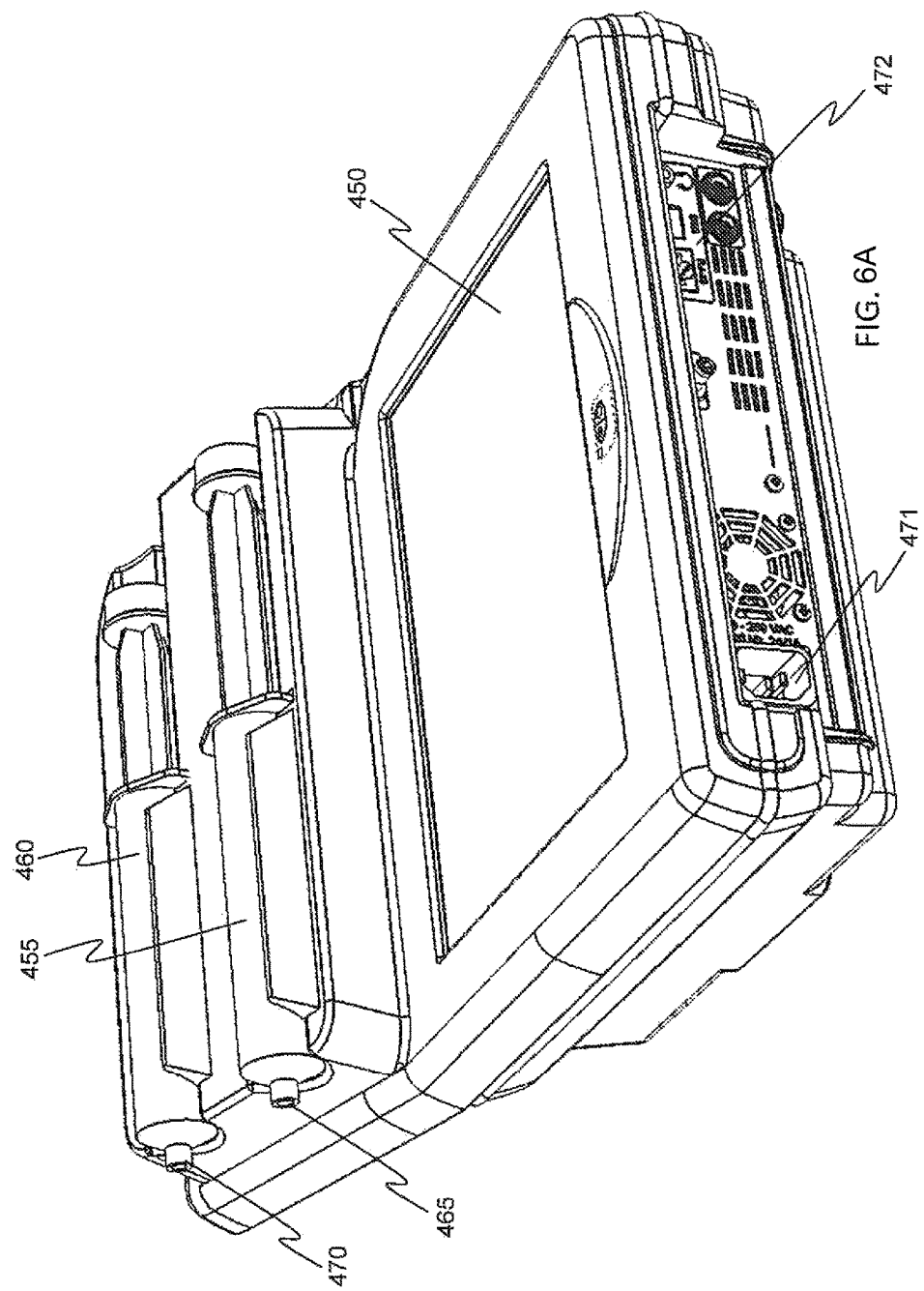

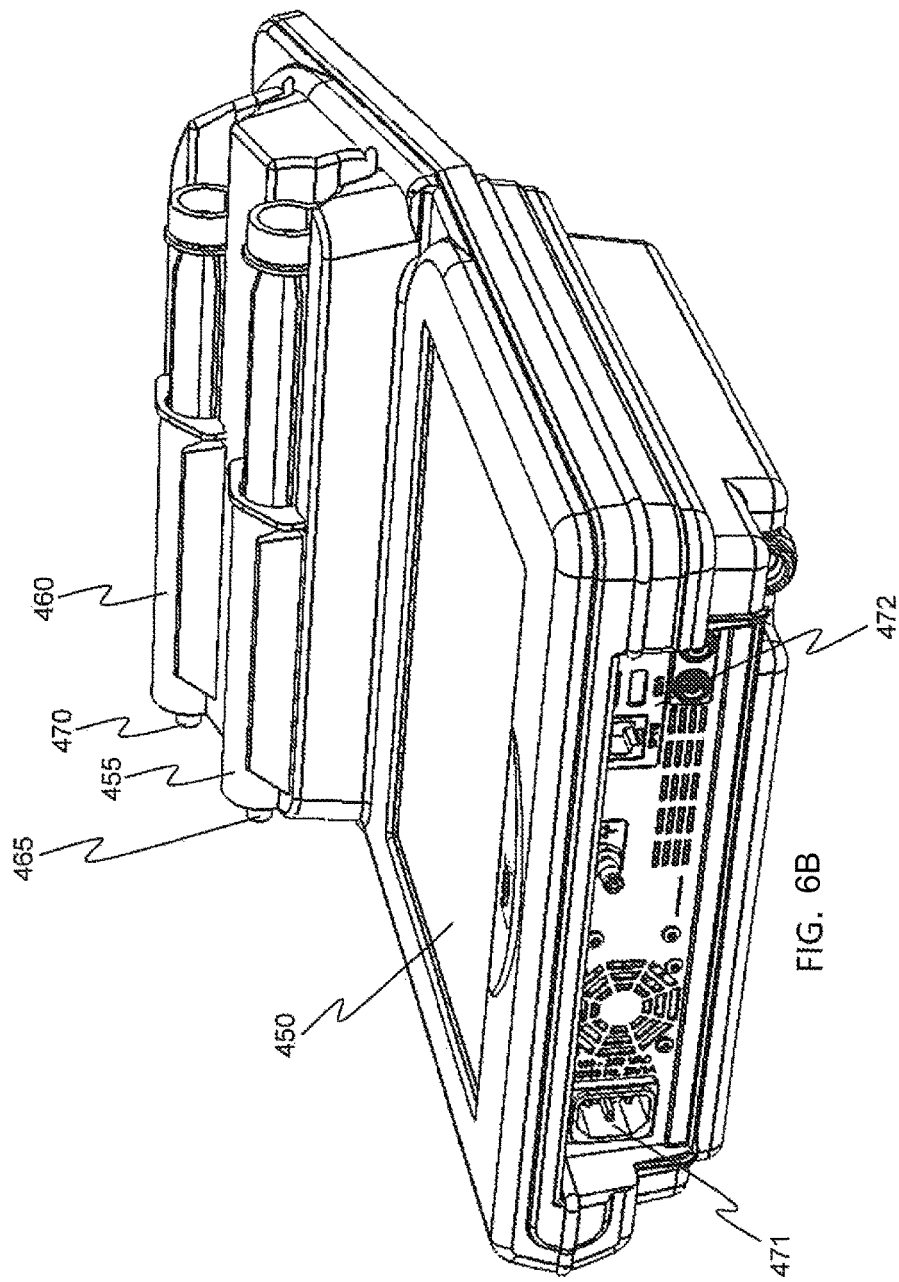

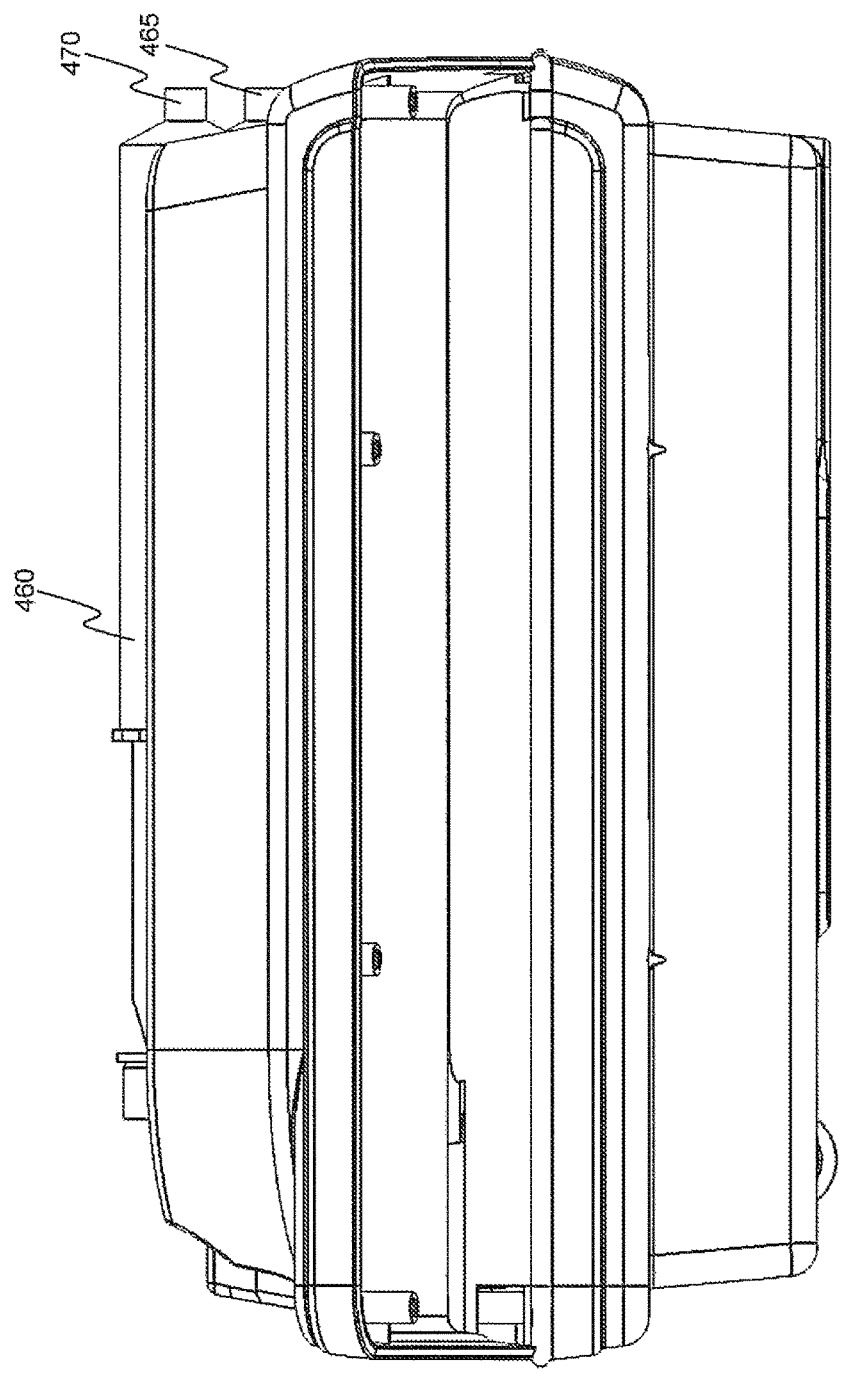

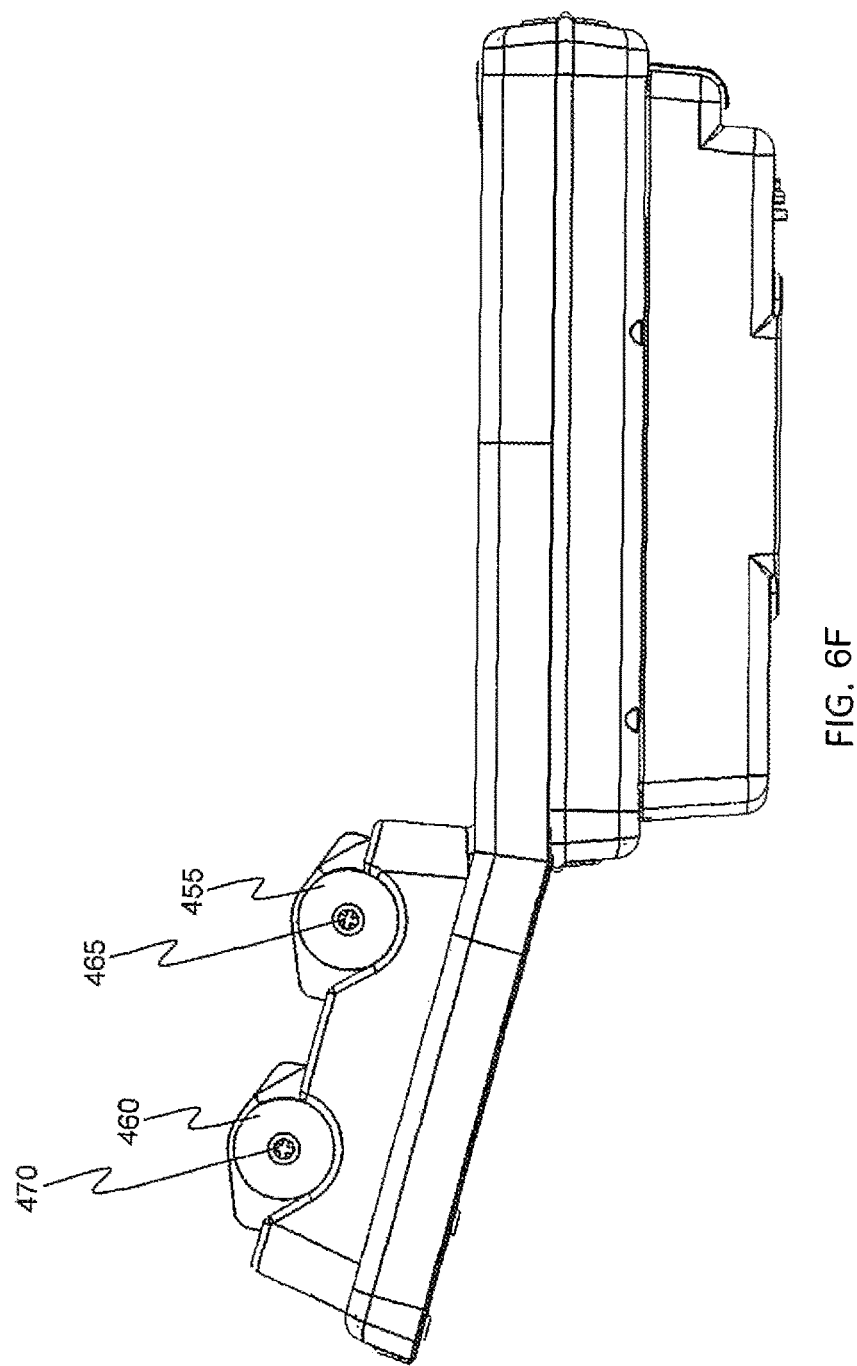

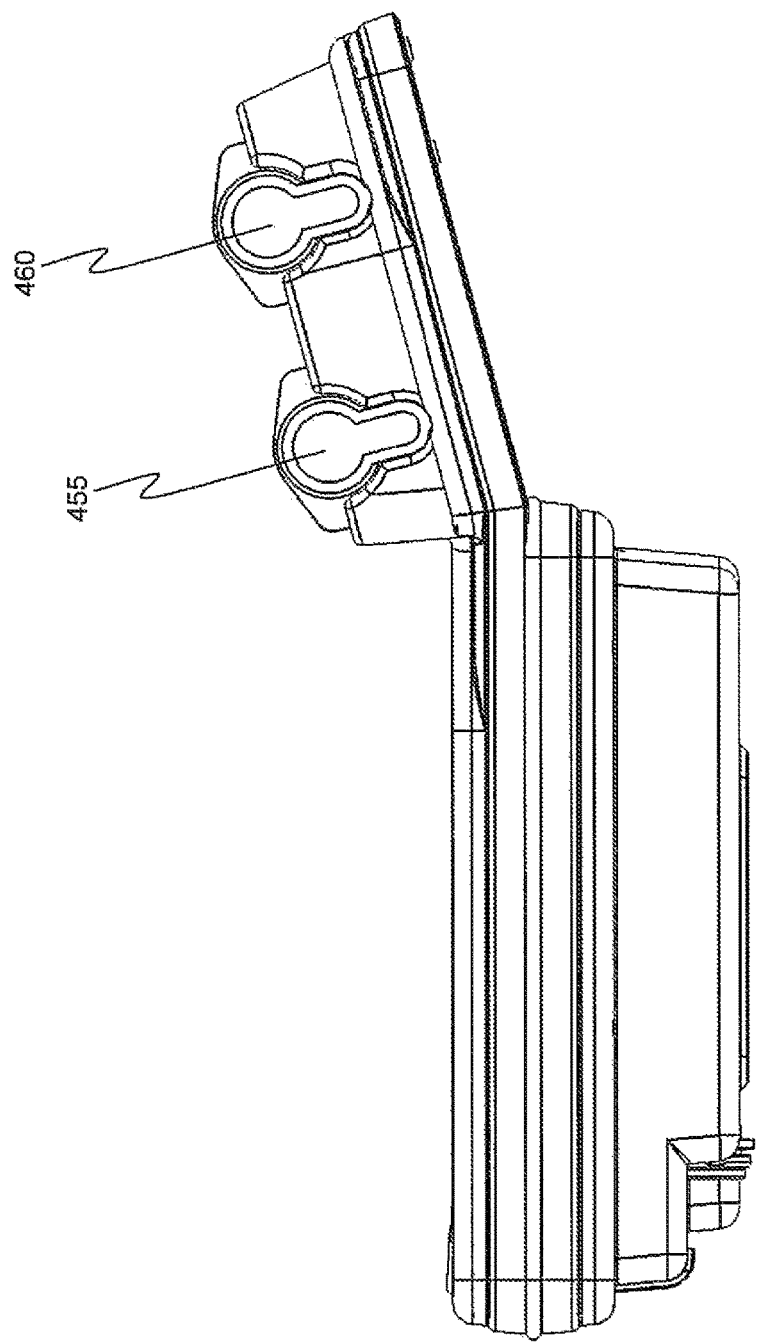

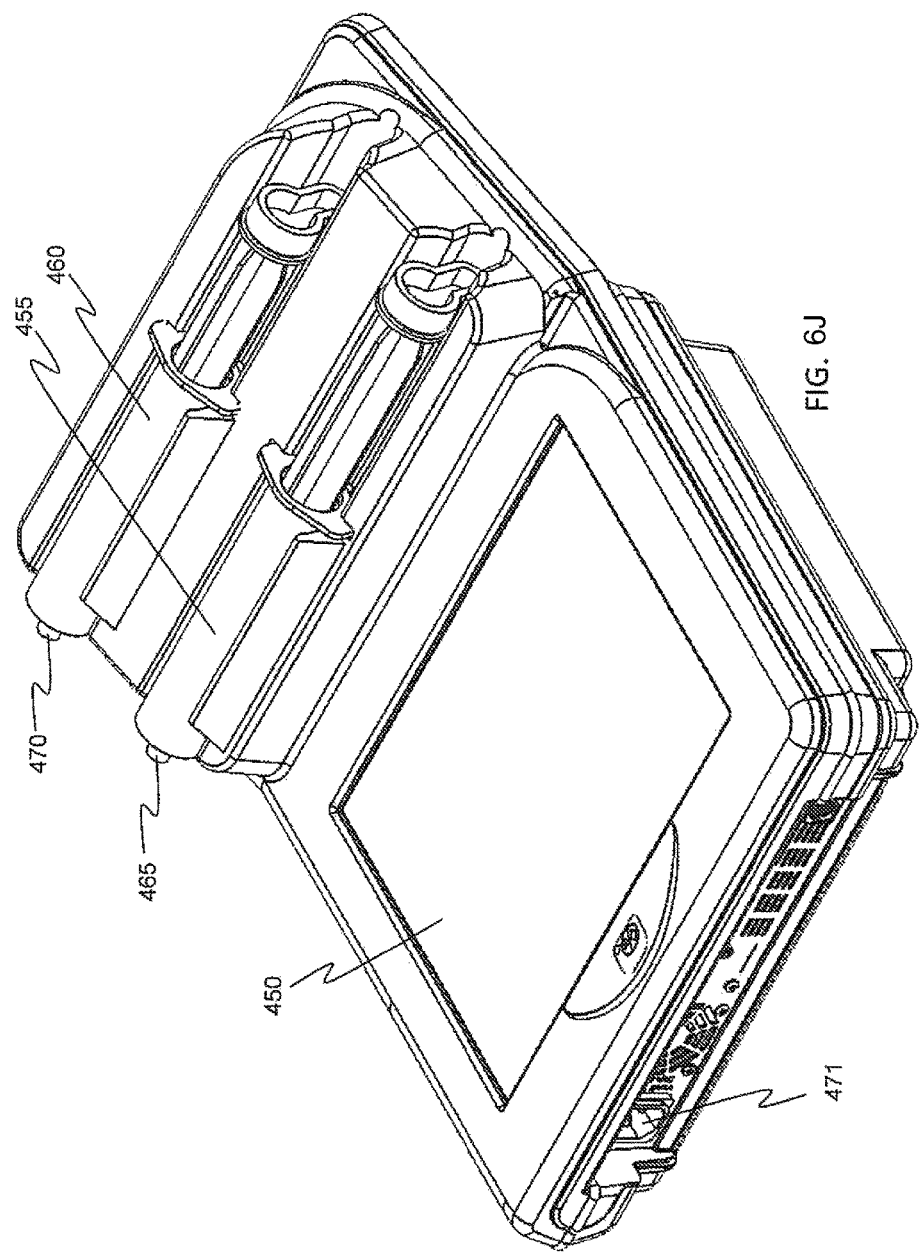

INTELLIGENT PHARMACEUTICAL DELIVERY SYSTEM WITH AUTOMATIC SHUTOFF AND METHOD OF USING

CROSS-REFERENCE TO RELATED APPLICATION

This application claims priority as a continuation-in-part of U.S. patent application Ser. No. 13/962,565, which was filed Aug. 8, 2013, and which claims priority to provisional U.S. Patent Application Ser. No. 61/680,888 filed on Aug. 8, 2012.

LICENSE RIGHTS-FEDERAL SPONSORED RESEARCH

The U.S. Government has a paid-up license in this invention and the right in limited circumstances to require the patent owner to license others on reasonable terms provided for by the terms of contract number W81XWH-11-C-0078 awarded by United States Army Medical Research Acquisition Activity (USAMRAA).

BACKGROUND OF THE INVENTION

1. Field of the Invention

The present invention relates to the monitoring and processing of signals, and particularly to the monitoring and processing of electrophysiological signals. More particularly, the present invention relates to processing electroencephalographic (EEG) signals to monitor brain function. Even more particularly, the present invention relates to a system and method for monitoring brain function and detecting burst suppression of physiological signals. Further still, the present invention relates to a system for controlling sedation or anesthesia for transportation or evacuation of the injured as well as closed-loop sedation or anesthesia at all echelons of care, including civilian and critical care facilities.

2. Technical Background

There exists an established and unmet need for providing enhanced capabilities in forward surgical, combat casualty care, and en-route care as well as in stationary civilian and critical care settings. Over the past 70 years, there have been attempts to use the electrical brain activity as a monitor of anesthetic depth. With increasing depth of sedation, the EEG shows a common progression from low-amplitude/high-frequency signal to high-amplitude/low-frequency signal, and finally to isoelectricity (i.e., flat signal characteristic of pharmacological coma), also known as burst suppression. Changes in EEG signals following the administration of drugs, ischemic episodes, changes in perfusion, etc., tend to occur rapidly. In order to detect them in a timely manner, trained EEG technologists must interpret the EEG signals in real-time and make rapid decisions based on their expertise. This is a particularly time consuming task, reserved only for a few specific clinical applications, such as the detection of ischemia during carotid endarterectomy, or the detection of ictal activity in the long-term EEG monitoring units in epileptic patients. Raw EEG signals are typically of little value to anesthesiologists and critical care physicians, as they lack the expertise and time required for their interpretation.

Since the late 1990s, a number of processed EEG monitors have been developed to simplify the interpretation of complex EEG signals, hence providing anesthesiologists with an additional, more direct means for drug effect assessment. The use of such monitors for drug titration to achieve optimal depth of anesthesia has been shown to improve the quality of anesthetic regimen, leading to a number of advantages directly related to patient outcome, e.g., (a) avoidance of excessive depth of anesthesia, (b) avoidance of intraoperative awareness, (c) reduction in post-operative recovery times, less post-operative and ICU delirium and less time spent on a ventilator in the ICU with lesser incidence of related pulmonary infections, (d) reduction in post-operative nausea and vomiting, and (e) reduction in duration of post-operative care units stay. Additionally, using such monitors, clinicians are able to manually adjust the amount of drugs administered in order to reduce the incidence of under- and over-dosing. In fact, the use of brain function monitors has been shown to help clinicians decrease the overall amount of drug administered to their patients, which in turn leads to faster wake up and discharge time, in addition to the other benefits for patient outcome listed above. Recent research has also shown that maintaining patients at too deep anesthetic levels is associated with an increased cognitive decline and post-operative mortality rate, which can be ameliorated with brain function monitoring.

At least one recent study has shown that a brain-monitored group showed a 78 percent reduction in patient recall of unpleasant experiences as compared to the standard practice group, along with an 18 percent decrease in cost of sedative drugs. In addition, the use of brain function monitors in chemically sedated patients has been found to facilitate the conflicting goals of maintaining sedation and safely interrupting sedation to perform a neurological examination. Today, there is a high incidence of oversedation in ICUs (40 percent to 60 percent of patients). Oversedation in the ICU is a serious problem, resulting in delayed weaning from mechanical ventilation, which lengthens ICU stay and significantly increases patient risks and healthcare costs. In 2003, prolonged mechanical ventilation (≥96 hours) occurred in about 300,000 cases, and accounted for nearly 7 million additional hospital days and $16 billion in hospital costs annually, projected to more than double by 2020.

Further, in spite of the advancements that have been made in anesthesia and sedation with the inclusion of brain monitoring, these systems are still relegated to mainly to surgical suites and the like. There is currently no sedation or anesthetic system utilizing brain monitoring which can be used in a setting other than a stationary one such as hospital operating room or similar facility.

In light of the above, it is therefore an object of the present invention to provide a system using brain function monitoring to enable safe anesthesia or sedation delivery in forward surgical, combat casualty care or en-route care as well as in stationary civilian and critical care environments. It is further an object of the present invention to provide a closed-loop anesthesia or sedation system capable of being applied even by a person with minimal training, and requiring no continuous human interaction or continuous human presence at the bedside. It is still further an object of the present invention to provide a system for closed-loop anesthesia or sedation which is capable of determining unsafe levels of anesthesia or sedation as well as unsafe brain activity, such as burst suppression, and controlling the level of anesthetic or sedative being delivered based on those determinations. It is yet another object of the present invention to provide a system and method for controlling anesthesia or sedation in the field, at the point of injury (POI), or during transport between the POI and upper echelons of care (e.g., hospital, surgical suite, etc.), in addition to all echelons of care, including civilian care facilities including but not limited to operating rooms, emergency rooms and intensive care units.

SUMMARY OF THE INVENTION

The present invention relates to the monitoring and processing of signals, and particularly to the monitoring and processing of electrophysiological signals. More particularly, the present invention relates to processing electroencephalographic (EEG) signals to monitor brain function. Even more particularly, the present invention relates to a system and method for. Further still, the present invention relates to a system for controlling sedation or anesthesia for transportation or evacuation of the injured as well as closed-loop sedation or anesthesia at all echelons of care, including civilian and critical care facilities. The present invention further relates to systems and methods for controlling anesthesia or sedation of a subject in stationary care facilities, such as the ICU or surgical settings, and possibly where the subject is on a ventilator. The system collects electroencephalographic (EEG) signals from a subject and utilizes various novel algorithms to analyze and quantify those EEG signals, or at least portions thereof, to monitor the subject. It should be noted that the EEG signals acquired by the system also contain electromyographic and electro-oculographic information. Many aspects of the subject's brain function can be monitored, including, but not limited to, monitoring the occurrence of seizures, occurrence of brain hypoperfusion or ischemia, alertness, sleep architecture and quality, cognition, memory, brain functional (or neuronal) connectivity, state of consciousness, EEG slowing, loss of EEG amplitude, cortical suppression, and the like. The system can also monitor the EEG for the presence of artifacts, like environmental extraneous noise, or physiological noise (e.g., muscle activity, movements, ocular activity, etc.).

Many embodiments of the system include a brain function monitor. The system or monitor may, in many embodiments be small, possibly miniaturized, optionally portable and possibly even disposable. The system or monitor should preferably be capable of use by even non-experts. By this, it is meant that a person should not be required to possess extraordinary or specialized medical training in order to be easily taught to use the system effectively and reliably. The system should therefore preferably be automatic in operation in a number of respects. First, the system should be capable of automatic calibration of its electronic circuits, their gains, filters and the like components and features in order to maintain the accurate signal acquisition and analysis without the need for human supervision of the instrumentation during the entire course of employment. Second, the system should preferably have automatic detection of poor electrode impedance, disconnected leads, and input signal quality; for example, the system should also be capable of detecting an imbalance in electrode impedances, physiological and environmental artifacts, and electrical and magnetic interferences and noise, including those due to electrostatic fields and discharges. Third, the system should preferably be capable of artifact detection and removal on one or more levels, so as to isolate, identify or recover for analysis that part of the signal which conveys meaningful information related to a subject's brain or cortical activity pertaining to: level of consciousness; occurrence of a seizure; level of sedation or depth-of-anesthesia; brain functional (or neuronal) connectivity that, for example, can be affected by diseases such as Parkinson's and Alzheimer's; occurrence of brain hypoperfusion; brain ischemia or impaired cerebral blood flow; brain death or dysfunction or impairment; brain metabolic demand; sleep disorders; sleep architecture and quality; alertness and cognition, memory; hypo- and hyperglycemia; psychiatric disorders such as depression, ADHD, autism, OCD, etc.; person's intentions, truthfulness or substance abuse; use in brain-computer interfaces such as for control of artificial prosthetics or dysfunctional body parts or objects or devices such as robots, game consoles, vehicles and the like; and use for detection or control of another person's or one's own thought or physiologic processes. Fourth, the system should preferably include output devices to provide outputs which result in visual and/or audible feedback capable of informing the user of the state of the patient related to quantification of brain or cortical activity, level of consciousness, occurrence of a seizure, level of sedation and the like as previously mentioned, at any time during the period of time that the system was monitoring the patient.

Preferably, the system should operate in real time. One example of real-time operation is the ability of the system to monitor the subject's physiological signals and provide quantitative analysis about the subject's status substantially simultaneously as the signals are acquired. Another example of real-time operation includes the ability to detect a seizure or brain dysfunction event, or other pathologic or nonpathologic brain event essentially as it is happening, rather than being limited to analysis that takes place several seconds, minutes or hours afterward. Preferably, by real-time detection, it is meant that the system operates to detect brain dysfunction or injury within 3 minutes of application of the system and/or occurrence of the dysfunction or injury. More preferably, the system operates to detect brain dysfunction or injury within 1 minute of application of the system and/or occurrence of the dysfunction or injury. Still more preferably, the system operates to detect brain dysfunction or injury within 30 seconds of application of the system and/or occurrence of the dysfunction or injury. Yet more preferably, the system operates to detect brain dysfunction or injury within 15 seconds of application of the system and/or occurrence of the dysfunction or injury. Even more preferably, the system operates to detect brain dysfunction or injury within 10 seconds of application of the system and/or occurrence of the dysfunction or injury. Still yet more preferably, the system operates to detect brain dysfunction or injury within 5 seconds of application of the system and/or occurrence of the dysfunction or injury. Still even more preferably, the system operates to detect brain dysfunction or injury within 1 second of application of the system and/or occurrence of the dysfunction or injury. Most preferably, the system operates to detect brain dysfunction or injury substantially instantaneously upon application of the system and/or occurrence of the dysfunction or injury. The system further operates in real-time with respect to monitoring of the subject's physiological signals such that there is substantially no lag or delay between the body's production of the signal, and the system's monitoring of the signal. The system described in this invention also preferably incorporates a number of unique features that improve safety, performance, durability, and reliability. The system should be cardiac defibrillator proof or other electric shock proof, meaning that its electrical components are capable of withstanding the surge of electrical current associated with the application of a cardiac defibrillator or other electric shock to a patient being monitored by the system, and that the system remains operable after sustaining such a surge. The system should have shielded leads so as to reduce as much as possible the effects of external electromagnetic interference on the collection of biopotentials or physiological signals from the patient being monitored by the system. The system should be auto-calibrating, more preferably capable of compensating for the potential differences in the gains of the different acquisition channels or in the impedances of the input electrodes.

Many embodiments of the brain function monitor include a sensing system comprising an electrode array or separate, individual electrodes, and in some embodiments a brain function monitor embedded within such an array. Preferably, at least two electrodes are utilized, comprising a monitoring electrode and a ground electrode. Alternatively, at least four electrodes may be utilized. In the four electrode array, preferably two electrodes are for monitoring EEG signals in the fronto-temporal region, one reference electrode is for providing a common reference signal, and one electrode is for grounding. Other electrode arrangements including larger number of electrodes, configurations, and placements are also contemplated for use with the system. Such electrode montages may or may not include a subset of 10-20 electrode placement system, or may go beyond it in both electrode locations and their number.

The electrodes used, when either separate electrodes or when part of an array, may be any of those commonly known in the art of EEG monitoring. The electrodes preferably do not require the application of conductive paste or gel. Therefore, the electrode lead or array preferably has any necessary conductive fluids pre-applied, or, more preferably, is a dry physiological electrode requiring no conductive fluid at all. Alternatively or in addition, the electrode is a wet-dry hybrid electrode as disclosed in U.S. patent application Ser. No. 13/110,505 (which application is entirely incorporated by reference) and the like. The electrode lead or array may be affixed to or embedded into a flexible, wearable substrate or apparatus, which can be applied directly to the injured subject's head or other body part, preferably the forehead. Preferably, the substrate is designed to be flexible, easy to don and doff, and disposable yet still resilient and capable of withstanding forces common in emergency settings such as excessive vibration, movement, electric noise, EMI, electric and mechanical shock, and the like, in addition to such forces present to a lesser degree in non-emergency settings. The apparatus may be secured about the subject's head or other body part by means commonly known to those in the art, including, but not limited to, a cap or other garment or garment attachment completely encompassing the subject's head, a strap that is secured by compression or elastic means, or may utilize common fastening methods such as hook-and-loop, belt-type, snap connectors, or the like. Additionally, or in conjunction with one of the above means, an adhesive layer may be used in conjunction with a wearable apparatus to further ensure a stable, secure placement of the electrodes. In a preferred embodiment, the flexible substrate is a small patch-type or adhesive bandage (BAND-AID-type) garment comprising an adhesive layer which, when applied to the injured subject's forehead, is capable of maintaining a secure placement with minimal shifting, drift, or other movement of the apparatus, for the entire length of time necessary for monitoring. The adhesive layer is also preferably capable of providing a secure, stable attachment to the subject in the presence of dirt, sweat, and other detritus which may be covering the subject's skin during application, without the need for washing, cleaning or otherwise preparing the area of application. Preferably, in the preferred embodiments where the electrode array is integrated in the flexible substrate, the patch is small and easily applied, and integrates the acquisition electronics in the form of a few integrated circuits (ICs) or chipsets whose role is to amplify, filter, digitize, analyze, process, store or transmit, optionally wirelessly, the EEG and QEEG analog or converted digital signals. Preferably, the integrated electronics are small and inexpensive, such that the array is cost effective, such that it can be fully disposed of after use, minimizing the need for maintenance and re-shelving, or refurbishing. Preferably, the flexible substrate also embeds a connector, which allows it to be connected to a monitoring device comprising a display device. Such monitoring/display device can provide the necessary power to the flexible substrate electronics, and can perform all other necessary processing and displaying of the results.

In many embodiments, the monitoring/display device is small, rugged, and easily transportable. Also optionally, both the device and the display device may be constructed to be inexpensive and disposable. In many embodiments, the display comprises internal memory for recording the monitored EEG signals and the various processed signals and calculated values, indices, and the like for later analysis by a trained clinician. Also, in many embodiments, the display comprises an internal power source, such as a battery, that powers the device during monitoring and is sufficient to provide power at least until the injured subject can be transported to an upper echelon care location, at which point the device could be removed, data could be uploaded, and the monitor and display could be discarded. The display is preferably capable of depicting a variety of outputs from the brain function monitor, including, but not limited to, EEG signal waveforms, processed EEG signal waveforms, indices calculated by the system to indicate various aspects of the subject's brain function (e.g., suppression, seizure occurrence, state of consciousness, sedation or anesthesia level, subject's pain or analgesia level, occurrence of traumatic brain injury (TBI), sleep architecture and quality, alertness, cognition, brain functional connectivity, brain hypoperfusion, ischemia or metabolic demand, memory, brain death or impaired function, hypo- or hyperglycemia and the like).

In other embodiments, the display device can be a portable medical-grade computer system, providing a graphical user interface to view in real-time the acquired EEG signals, and review all processed quantitative EEG parameters.

Also, in some embodiments of the present invention, the display device or the device itself can communicate, optionally wirelessly, with other medical equipment, such as life signs monitors and drug delivery systems, or transmit the information to internet or upload it to a cloud, preferably in real time, for remote review, analysis or storage and the like. In some embodiments, the display device or the device itself can directly control one, two or more infusion pumps to deliver intravenous drugs to the patient. In one embodiment, a single infusion pump may be used to automatically adjust the infusion rate of a drug to provide and maintain a stable and suitable concentration of said drug in the injured subject's blood plasma. In many embodiments, the drug provided is a sedative or anesthetic drug, which is infused to maintain the subject at a stable sedation or anesthesia level with minimal or no human supervision. In many embodiments, alternatively, or in conjunction with the sedation or anesthetic drug, at least one (additional) infusion pump may be provided for infusion of analgesic medication to provide a stable and suitable level of pain relief or analgesia to the injured subject. In yet other embodiments, a third pump may be used to provide muscle relaxation medication. In other embodiments, additional pumps may be used to provide various therapeutic substances such as fluids, insulin, heart rate and blood pressure regulating medications, anti-anxiety drugs, various antagonists and the like. In all embodiments, the patient's reaction to these drugs and substances is monitored via the brain monitoring system, which includes the electrode array, the device and the display device described above, which further could be integrated in a single system, potentially implantable. Such a system can enable the use of Total Intravenous Anesthesia (TIVA); or the use of other patient management therapies (e.g. fluid management, intravenous sedation, diabetes management, epilepsy management, pain management, etc.); or the delivery of other therapeutics such as electric shocks and signals (e.g., ECT, DBS), mechanical shocks and signals, chemical substances and signals, light signals, sound signals; or the use of brain-computer interface; in situations where it was not safe or possible to use such technique before.

In yet other embodiments, the display device or the device itself can directly integrate an infusion mechanism to deliver 1, 2 or more intravenous drugs. Such system, referred in the following as the Integrated Monitoring and Infusion System (IMIS), may optionally be designed and constructed to be small, lightweight, and easily portable without providing cumbersome bulk or awkwardness to the person carrying it, though may preferably be a typical infusion system used in stationary or semi-stationary clinical care applications. The IMIS is also preferably constructed to be rugged and able to withstand forces and shocks attendant to the circumstances in which it is deployed (such as but not limited to battlefield, transport, etc.). In many embodiments, the IMIS comprises at least one syringe infusion pump for automatically adjusting infusion rates of a drug to be administered to the injured subject attached to, embedded in, or otherwise integrated with a portable enclosure or modular system or case. The infusion pump preferably is used to provide and maintain a stable and suitable concentration of at least one drug or substance to the injured subject. In many embodiments, the drug provided is preferably a sedative or anesthetic drug, which the IMIS infuses and monitors to maintain the subject at a stable sedation level with minimal or no human supervision. In many embodiments, alternatively, or in conjunction with the sedation or anesthesia drug, at least one additional infusion pump may be provided for infusion of analgesic medication to provide a stable and suitable level of pain relief or analgesia to the injured subject. In many embodiments, the IMIS is used for sedation and/or pain management purposes to stabilize the patient for en-route care provided while waiting and/or during transport from the point of injury to a location of higher echelon care as well as at all echelons of care including civilian care facilities.

In many embodiments, the IMIS embeds a control algorithm which utilizes input from the brain function monitor, and optionally from a user, to calculate preferred infusion rates of the sedation or anesthetic and/or analgesic drugs. For example, in many embodiments to control algorithm calculates preferred infusion rates based at least in part on a calculated index (e.g., $WAV_{CNS}$) in combination with user inputted data specific to the subject (e.g., weight, height, age, sec, etc.). Preferably, the algorithm performs these calculations substantially in real-time to provide the necessary modifications to the drug infusion rates immediately. In some embodiments the IMIS embeds a control algorithm which utilizes input from the brain function monitor to calculate preferred infusion rates of other therapeutic drugs and substances for patient management (e.g., fluids, insulin, heart rate and blood pressure regulating medications, anti-anxiety drugs, various antagonists and the like), or to control the delivery of other patient management and therapy solutions that were previously mentioned and that not necessarily utilize only infusion but by other avenues including but not limited to gaseous administration and absorption, and utilizing other therapeutic signals and methods (electrical, mechanical, etc.).

The IMIS device may be operated manually or in a semi-closed loop or closed-loop manner. In one preferred embodiment, the IMIS and the associated electrode array are used in the field, on injured subjects, to deliver and maintain a proper level of sedation and analgesia, or other therapeutic substances and methods, while waiting for medical evacuation. In other embodiments, the IMIS can be used in medical evacuation vehicles, for en-route care, to control the level of stress and pain of the patient, or to provide other substances and therapies (e.g., management of fluids, insulin, heart rate and blood pressure regulating medications, anti-anxiety drugs, various antagonists, as well as electrical, mechanical, sound, light and the like therapeutic signals) and keep him or her safe or comfortable. In yet another preferred embodiment, the IMIS is used in the emergency room or other clinical setting and the like in higher echelons of care facilities, to provide sedation or anesthesia or other therapies for patient management. In yet another preferred embodiment, the IMIS is used in the peri-operative environment to provide sedation or anesthesia or other patient management therapies to the patient. Finally, in yet other embodiments, the IMIS can be used in Intensive Care Units (ICUs), to provide sedation or other patient management therapies to the patient and help through his or her recovery process.

The brain function monitor, IMIS, the combination thereof, and the methods for using these systems are preferably designed to be applicable for in-the-field uses as well as stationary, semi-stationary or traditional care environments. In-the-field is meant to be any application, setting, location or circumstance where the subject is injured and does not have immediate, ready access to sophisticated, formal medical care settings. By way of example, and not meant to limit the applications of the present invention, the in-field portable device and methods described herein can be used in battlefield, professional/recreational/amateur sports, or other entertainment (such as concert) venues, or may be utilized by first responders, medical transport and/or evacuation, security, police, or the like in emergency or other injury situations. In other words, the present invention's device(s) and methods are contemplated to be used for many injuries even those with a sudden onset, in order to provide monitoring, assessment, diagnosis, anesthesia, sedation, and/or pain management until the injured subject can be transported to an end care location of upper echelon medical care with equipment that would supplant this portable, disposable device and the methods for its use. Yet, it should be noted that the device discussed in the present invention can also be designed and used in all clinical environments and echelons of care where the patient is stationary or semi-stationary in location. As such the devices and systems of the present invention should at least be portable in the sense that they can be moved readily along with or separate from the subject, for example between rooms or departments of a critical or stationary care facility.

Other embodiments similar to those listed above may optionally have one or more of the following features: a display weight of less than 4 ounces; the display showing either or both of raw EEG data and processed data about patient brain state; manual enablement/disablement of automated drug administration; measurement of fronto-temporal cortical activity solely to determine whether drugs are needed; built-in infusion and monitoring control algorithms (as discussed later in this application); adaptive monitoring features that provide for use to reduce the risk of sedative overdose in patients with high blood loss; the monitoring system being disposable in its entirety; a paper battery suitable for providing adequate power for the application over adequate measurement/analysis times of at least 2, and preferably 3, and more preferably 4 hours; a display the size of a credit card; a memory to store the signal(s) for analysis later; the capability to automatically detect seizure, suppression, or unconsciousness; the display being capable of displaying indices, warnings, or other messages for the user; portable and ruggedized construction permitting use on the battlefield, at a sporting event, by emergency first responders, and at schools and workplaces; a battery integrated into display such that the display can be traded off and used for later data analysis, while permitting continued monitoring by swapping out with a new display; and an internal memory and USB interface built into the display permitting the display to be plugged into a computer for easy and fast data transfer, reprogramming, software or firmware updates, etc.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

Various embodiments of the present invention may gain the benefit of many existing systems, methods and devices, whose patent applications are hereby incorporated by reference, including: systems and methods for the detection of seizures and other ictal activity (U.S. patent application Ser. No. 12/259,852; U.S. patent application Ser. No. 13/731, 315); various varieties of electrodes and sensors (e.g., U.S. patent application Ser. No. 13/110,533 U.S. patent application Ser. No. 13/899,632); systems and methods for acquiring biosignals in the presence of high-frequency interference (U.S. patent application Ser. No. 11/827,906; U.S. patent application Ser. No. 13/335,256); systems and methods for detecting burst suppression of physiological signals (U.S. patent application Ser. No. 11/827,906; U.S. patent application Ser. No. 13/216,755); and systems and methods for denoising large-amplitude artifacts in electrograms using time frequency transforms (U.S. patent application Ser. No. 10/968,348), as well as issued patents, which are also hereby incorporated by reference, including U.S. Pat. No. 7,603,168 disclosing closed loop systems and processes, U.S. Pat. No. 7,672,717 disclosing artifact detection, and U.S. Pat. No. 7,373,198 disclosing quantification indexes for cortical activity.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in and constitute a part of this specification. The drawings illustrate various embodiments of the invention and together with the description serve to explain the principles and operation of the many embodiments of this invention.

BRIEF DESCRIPTION OF THE DRAWINGS

FIGS. 6A-6J. Various views of one embodiment of the IMIS including A) front-left perspective view; B) front-right perspective view; C) back perspective view; D) front isometric view; (E) back isometric view; F) left isometric view; G) right isometric view; H) top isometric view; I) bottom isometric view; and J) isometric view.

FIGS. 7A-7H. Various screenshots of one embodiment of the present invention including: A) a screenshot of an "Effect" screen; B) a screenshot of a "Pumps" screen; C) another screenshot of a "Pumps" screen; D) a screenshot of a "PCLC" screen; E) another screenshot of a "PCLC" screen; F) another screenshot of a "Pumps" screen; G) a screenshot of a "patient information screen; and H) another screenshot of a "Patient information" screen.

DETAILED DESCRIPTION OF THE PREFERRED EMBODIMENTS

Figure 1A:
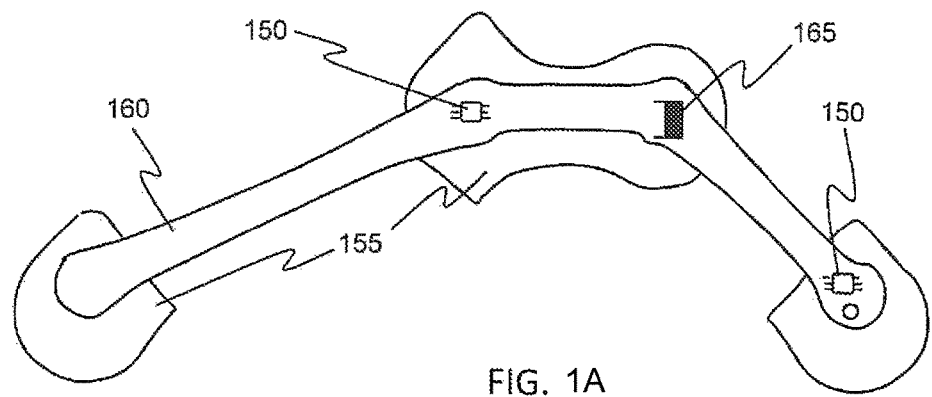
FIG. 1A. Depiction of one embodiment of the flexible substrate with electrode array.

The present invention relates to the monitoring and processing of signals, and particularly to the monitoring and processing of electrophysiological signals. More particularly, the present invention relates to processing electroencephalographic (EEG) signals to monitor brain function. Further still, the present invention relates to a system for controlling sedation or anesthesia for transportation or evacuation of the injured as well as closed-loop sedation or anesthesia at all echelons of care, including civilian and critical care facilities.

For the present invention, the subject whose EEG signal is being measured can be any type of animal, preferably a mammal, most preferably a human. Also, caregiver and clinician are understood to include not only those skilled in the use of EEG equipment and methodologies, such as doctors, physicians, anesthesiologists, EEG technologists, emergency response personnel, nurses, and the like. The device and methods are designed to be used and performed, respectively, largely by untrained or minimally trained personnel, until the injured subject may be transported to a clinician as described above for more acute and skilled care in proper facilities or locations.

The various embodiments of the present invention are preferably one or more of portable, ruggedized, disposable, and capable of rapid application and use. By "portable" it is meant that a single embodiment is light enough in weight and compact enough in size to be carried in a small handheld and hand-carried case that may be carried easily by a single person and applied to a subject or patient without impeding the subject's easy and safe transport. Preferably, this means that the subject is completely untethered, except, in some embodiments, to a small monitor and/or therapy device which can be attached to the subject, the subject's clothing or gear, or the subject's gurney, stretcher, or bed and easily moved along with the subject. Preferably, the entire system weighs less than 75 lbs. More preferably, the entire system weighs less than 60 lbs. Still more preferably, the entire system weighs less than 50 lbs. Yet more preferably, the entire system weighs less than 40 lbs. Even more preferably, the entire system weighs less than 25 lbs. Still more preferably, the entire system weighs less than 20 lbs. Yet more preferably, the entire system weighs less than 15 lbs. Even more preferably, the entire system weighs less than 10 lbs. By "ruggedized" it is meant that the embodiment has features that harden it to mechanical and electrical shocks and dust/fluid ingress, etc., as described elsewhere in this application which permit the embodiment to be transported and used in emergency settings. "Disposable" is defined by a number of factors as discussed elsewhere in this application. "Rapid application and use" means that the system or apparatus embodiment can be taken from a storage or transportation configuration, applied to a subject or patient, and used for measurement, monitoring, analysis and/or therapy in less than ten minutes. More preferably, application can be performed in less than one minute. More preferably, application can be performed in less than thirty seconds. Still more preferably, application can be performed in less than ten seconds. More preferably still, application can be performed in less than five seconds. Such rapid applications can be realized by providing a monitor embodiment as a simple adhesive patch that is peeled from a backing and applied to a patient or subject's forehead, whereupon the monitor embodiment automatically activates, self-calibrates, and begins measurement, monitoring, analysis, and/or therapy.

Various embodiments of the methods of the present invention include one or more of the following steps, and variations thereof. These steps include, but are not limited to, monitoring a subject with a brain having a left hemisphere and a right hemisphere, by connecting the subject to a brain function monitoring device with at least one electrode lead comprising at least one measurement electrode and at least one reference electrode, the at least one electrode lead comprising at least one EEG electrode, having a signal associated therewith, positioned on a subject's head to monitor activity of the subject's brain, the reference electrode comprising at least one EEG electrode, each electrode providing an EEG signal. Alternatively, monitoring of the subject's brain function can be performed with at least one electrode array comprising a plurality of measurement EEG electrodes and at least one reference electrode, each of the plurality of EEG measurement electrodes having a signal associated therewith.

Similarly, various embodiments of the device of the present invention include one or more of the following components, and variations thereof. These elements include, but are not limited to, an electrode array(s), a display device, an anesthetic or sedation infusion and monitoring system, a processor, which may embed signal processing algorithms, and/or a control algorithm(s) for controlling drug infusion, and drug infusion device(s).

All embodiments of the present invention involve acquiring an electroencephalographic (EEG) or functionally equivalent signals from a subject or a patient. In acquiring EEG signals, electrodes can be placed at various locations on the subject's scalp in order to acquire EEG or brain wave signals. Common locations for the electrodes include frontal (F), temporal (T), parietal (P), anterior (A), central (C) and occipital (O). If the particular embodiment utilizes an array of electrodes, the array may contain electrodes positioned at one or several of these or other locations. Preferably for the present invention, at least one electrode is placed at or near the fronto-temporal region of the subject's brain, on the subject's scalp. Additionally, preferably at least two electrodes are used, one signal electrode and one reference electrode; if further EEG or brain wave signal channels are desired, the number of electrodes required will depend on whether separate reference electrodes are used or, instead, a single reference electrode is used for multiple channels. The step of monitoring brain function includes using at least one sensor, including physiological signal sensors, to measure a subject's brain wave signals over a period of time. The brain wave or EEG signals can be obtained by any method known in the art, or subsequently developed by those skilled in the art to detect these types of signals. Sensors include but are not limited to physiological signal sensors such as electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subject's scalp.

The electrodes may be affixed to or preferably embedded into a flexible, wearable apparatus which can be applied directly to the injured subject's head, preferably the forehead. Preferably, the wearable apparatus is designed to be flexible, easy to don and doff, and disposable yet still resilient and capable of withstanding forces common in emergency settings. As used in this application, an "emergency setting" is limited to places and events outside of hospitals, clinics, and other places where trained medical professionals are close at hand. Exemplary emergency settings include battlefields; settings of vehicle or construction accidents; sites of mass casualty, terrorist attack, or natural or industrial disaster; schools; sports fields and arenas; shopping areas, pedestrian areas, and other places generally open to the public; workplaces, homes, and residences, and the like. A staffed and equipped emergency room is not an "emergency setting." Forces common in emergency settings include those previously mentioned as well as those associated with roughly ported or dropped—accelerations and shocks uncommon in hospital and emergency room settings and which would damage or destroy equipment designed for use in a hospital. However, it is to be noted that the current invention is not limited to use in emergency settings only. The apparatus may be secured about the subject's head by means commonly known to those in the art, including, but not limited to, a cap or other garment completely encompassing the subject's head, a strap that is secured by compression or elastic means, or may utilize common fastening methods such as hook-and-loop, belt-type, snap connectors, or the like. Additionally, or in conjunction with one of the above means, an adhesive layer may be used in conjunction with a wearable apparatus to further ensure a stable, secure placement of the electrode lead or array. In a preferred embodiment, the flexible apparatus is a small patch-type garment comprising an adhesive layer which, when applied to the injured subject's forehead, is capable of maintaining a secure placement with minimal shifting, drift, or other movement of the apparatus, for the entire length of time necessary for monitoring. The adhesive layer is also preferably capable of providing a secure, stable attachment to the subject in the presence of dirt, sweat, and other detritus which may be covering the subject's skin during application, without the need for washing, cleaning or otherwise preparing the area of application. Preferably, in preferred embodiments where the electrode array or sensing system is affixed to or embedded in a patch-type garment, the patch is small and easily applied. Preferably, the surface area of the sensing system and/or patch, including electrode array(s) is less than 10 square inches. More preferably, the surface area of the sensing system and/or patch is less than 8 square inches. Even more preferably, the surface area of the sensing system and/or patch is less than 6 square inches. Still more preferably, the surface area of the sensing system and/or patch is less than 4 square inches. Yet more preferably, the surface area of the sensing system and/or patch is less than 2 square inches. Other similar methods of acquiring physiological signals may be used in the present invention which are known to those skilled in the art for acquiring signals such as electrocardiography (ECG), electrical impedance tomography (EIT), electromyography (EMG) and electro-oculography (EOG).

In order to obtain a good EEG or brain wave signal it is desirable to have low impedances for the electrodes. Typical EEG electrodes connections may have impedance in the range of from 5 to 10 kilo-ohms. It is, in general, desirable to reduce such impedance levels to below 2 kilo-ohms. Therefore a conductive paste or gel may be applied to the electrode to create a connection with impedance below 2 kilo-ohms. Alternatively, the subject's skin may be mechanically abraded, the electrode may be amplified using active circuitry, or a micro-penetrating dry electrode may be used. Dry physiological recording electrodes of the type described in U.S. Pat. No. 6,785,569 can be used. U.S. Pat. No. 6,785,569 is incorporated by reference. Dry electrodes provide the advantage that there is no gel to dry out, no skin to abrade or clean, and that the electrode can be applied in hairy, sweaty, and/or dirty areas such as the scalp, particularly for in-the-field applications.

It is also contemplated that the electrodes may be nothing more than electrode pads consisting of a thin conductive coating (e.g., a coating of silver or other metal) printed onto the underside of a flexible substrate. In such an embodiment, the flexible substrate preferably has flexible printed circuit board (PCB) traces embedded in it to carry signals acquired by the electrodes or electrode pads to processing electronics. Although "dry" in the sense that these simple electrodes have no electrode gel, such electrodes are to be distinguished from the dry electrodes mentioned above, and are not referred to herein as dry electrodes.

Almost all embodiments of the present invention include a display. Preferably, the display provides a touch-screen interface for the caregiver to interact with the system, although other control means such as analog buttons, or a combination of screen output and analog or digital controls may be used. In some embodiments, the display may simply integrate light-emitting diodes (LEDs) as a means of displaying visual information to the user. In other embodiments, the display may be more complicated, such as a touch screen, which also provides a direct user interface. Also, a processor may be integrated in the display unit to process the EEG signals. This processor can be based on a reduced instruction set computing (RISC) microprocessor, or a digital signal processor (DSP). Preferably, the processor is a microprocessor sufficiently miniaturized to fit into the small device or display and provides little or no bulk or weight to the device. Further, the processor embeds algorithm(s) for making particular determinations, e.g., presence of seizure activity, EEG slowing, low cortical activity level, presence of EEG amplitude loss or cortical suppression. In a particular context-of-use, such as a far forward deployment, a trigger in any of these endpoints may point to the presence of abnormal function or injury, such as TBI. In particular, the determinations are made based on at least one of several algorithms coinciding with the above described methods and steps, including, but not limited to, seizure detection, cortical suppression detection, EEG slowing detection, cortical activity level measurement, and the like. The algorithms can be used on a single EEG channel, two channels, or more, as needed. Processed information from two or more channels may be combined to improve the determination of the presence or absence of abnormal activity or injury. Other algorithms may be provided, including, but not limited to, those for providing measures such as spectral edge frequency (SEF) or the median edge frequency (MEF), or other methods based on entropy and/or bispectral analysis.

In many embodiments, the display also optionally contains internal memory for storage of acquired and/or processed EEG signals, calculated data (e.g., EEG events such as seizure or suppression, indices, alerts, and the like), and/or logistical data (e.g., time, location, GPS coordinates, and the like). The internal memory may consist of a removable flash memory card such as an SD, miniSD, microSD, MMC, CompactFlash, or the like. Alternatively, or in addition, the display may contain an internal, non-removable memory for such storage. In such embodiments, the non-removable memory may be read by connecting the display to another device by means of a cable, or by virtue of an incorporated USB-type attachment that may fold out of the display to be inserted directly into another device. Some embodiments may provide both non-removable and removable memory to provide redundancy in the data storage in the even that one of the memory components is destroyed, damaged or lost. Data from the memory may in some embodiments be transmitted by wired or wireless transfer using any of the protocols described in this application or known to those skilled in the art.

The display further optionally comprises an internal power source. Such internal power source furthers the ease and simplicity of use of the device by removing the need for power cables or cords, as well as the external power source. This also increases the portability of the device. Such internal power source may be a battery of any type known to those in the art that is suitable for the type of applications envisioned for the device, and that contain sufficient life to power the device from deployment until the subject is delivered to a location of higher echelon care and can be monitored by more permanent, robust equipment and caregivers. In addition to a battery, the display may incorporate a source of renewable or regenerative power, such as solar power to maintain the life of the display.

In some embodiments of the present invention, the physiological signal monitor includes the electrodes, display and signal acquisition electronics constitute the physiological signal monitoring component, and may further include an automatic, continuous electrode impedance checking ability. Traditional impedance checking techniques require the monitoring system to halt biosignal acquisition and monitoring in order to check and measure the impedance of a given electrode. However, continuous impedance checking, in the context of the present invention, means that impedance can be measured simultaneously with continued, uninterrupted monitoring and acquisition of the desired biosignal. In other words, the acquisition function of an electrode does not need to be halted in order to check the impedance of any given electrode. In order to continuously check electrode impedance, such embodiments require an alternating current source generator that is capable of progressively increasing and decreasing electrical current into the individual measurement electrodes. Preferably, the current supplied to the measurement electrodes is supplied at a known amplitude and frequency. Also preferably, the frequency of the supplied current is outside of the biological frequency of the physiological signal being monitored (herein referred to as the bio-band). Supplying the current outside the biological frequency for the signal from the electrode being measured prevents interference with the diagnostic signal—preventing perturbation of the measured physiological signal. For example, the typical biological frequency (bio-band) of EEG signals is from about 0.5 Hz to about 70 Hz, but can expand to between 0.125 Hz to about 120 Hz. Meanwhile, the typical bio-band for EMG signals ranges from about 30 Hz up into the kilohertz range. The maximum level of the impedance measurement current supplied further depends on the electrical instrumentation utilized as well as legal limits set with regard to patient care, depending on the application. The supplied current must be within the limits of the instrumentation so as not to overload the amplifiers and cause the system to fail. Also, regulations limit currents supplied to the human body to levels below 10 microamps.

Once the electrical current being supplied to the first measurement electrode has reached the predetermined maximum stabilized current, the voltage resulting from the supplied current is measured across the system. The voltage and current values are known to the system and are used to calculate an electrical impedance of the first measurement electrode. Preferably, this voltage measurement and impedance calculation is carried out over a period of time of one cycle depending on the frequency. The resultant impedance value calculated for the first measurement electrode is compared against a threshold value to determine whether the electrode is providing as clear a signal as possible for accurate EEG or other physiological signal display. This threshold value is determined by the application as to the sensitivity necessary to provide a good physiological signal. If the electrical impedance calculated in the first measurement electrode is too high, then a technician or operator is notified and he or she decides what type of action is required to renew the quality of the signal. This process is described in greater detail in U.S. Patent Application Publication No. 2011/0295096 A1, which is incorporated by reference.

Additionally, in many embodiments, the physiological signal monitor should have an artifact detection and/or removal system which differentiates between a normal (or abnormal) physiological brain activity and artifacts or noise caused by various sources of interference. The process of artifact detection is described in greater detail in U.S. Patent Publication No. 2011/0295142 A1, which is incorporated by reference.

Further, many embodiments of the present invention provide a cortical suppression detection function to monitor and notify the user when a subject's brain function is suppressed below a threshold level, or when the EEG signal amplitude drops below a certain level. Suppression may be indicative of severe brain trauma such as traumatic brain injury (TBI), over-sedation or anesthesia over-dosing, or the like. In order to provide the suppression detection function, such embodiments may involve computing the first derivative of the physiological or sensor signal. Most embodiments utilize the first derivative, though some embodiments may use a higher derivative. Utilizing the first derivative rather than the raw (or filtered) EEG signals has been shown to remove baseline wandering and thus renders the analysis more accurate and reliable. The step of computing the first or higher derivative of the signal is performed on a processor, in real time, and substantially at the same time as the signal is being acquired. Substantially at the same time means that immediately as the signal is acquired by the circuitry and apparatus described above, the processor computes the appropriate derivative of that signal. Once the desired level of derivative has been computed, an epoch of predetermined size of the derivative of the EEG signal is analyzed using at least one suppression detection parameter, the at least one suppression detection parameter being used to detect suppression in the EEG signal. The suppression detection measure can be virtually any type of operator or algorithm which is capable of detecting the drastic changes in the EEG signal which may be representative of burst and/or suppression periods. Such suppression detection measures may include, but are not limited to the median absolute value, the peak-to-peak time measurement, root mean square (RMS), spectral measures, entropy measures, energy operators, and the like. Preferably, at least one suppression detection measure used is the median absolute value of the first derivative of the EEG signal. The median absolute value is a robust measure of the rate of change of EEG, is less sensitive to outliers, and corresponds with the visual recognition rules of suppression detection. Thus, as the EEG, or other physiological signal, is acquired, the processor first calculates the desired derivative of that signal, and essentially simultaneously computes at least the median absolute value of that first derivative signal. Next, such embodiments utilize the above calculated suppression detection measure(s) (e.g., median absolute value) for the detection of suppression periods in the EEG signal. If the above calculated suppression detection measure is below a predetermined threshold for a predetermined amount of time, then that particular epoch is determined to be suppression. Some embodiments include a step in which artifacts are detected and identified, and are not counted as periods of burst activity. These artifacts may be those that were not detected by the front-end filtering, or new additional artifacts that corrupt the signal after initial filtering. In this optional step, the present invention differentiates between such artifacts and burst activity. This means that the system does not count an aberrant artifact as burst activity and thus effect the detection of burst and suppression periods and their durations. This is another step to increase the accuracy of the invention in environments that create artifacts in the EEG signal. Some embodiments of the present invention further include a step by which the thresholds used for detecting a burst or suppression period are automatically relaxed or tightened based on environmental factors. For example, if the signal contains a particularly strong or high amplitude period of burst activity, the threshold may be relaxed so the results of the detection methods are not artificially skewed or misidentified. This process is described in greater detail in U.S. patent application Ser. No. 13/216,755, which is incorporated by reference.

Various embodiments of the present invention specifically rely on detection of suppression of the physiological signal. Burst suppression detection is generally based on detection of periods of high activity alternating with periods of no activity of a physiological signal. Burst suppression is most typically discussed in regards to EEG signals, though other physiological signals exhibit the same or similar characteristics under certain conditions as well. Therefore, burst suppression is most notably useful in EEG analysis, but the same principles can be applied to most physiological signals, such as EKG, EMG, EOG, and the like. One step in suppression detection involves computing with a processor, substantially at the same time as the signal is acquired, the first derivative of the physiological or sensor signal. Most embodiments utilize the first derivative, though some embodiments may use a higher derivative. Utilizing the first derivative rather than the raw (or filtered) EEG signals has been shown to remove baseline wandering and thus renders the analysis more accurate and reliable. In addition, the surface EEG signals are the time-varying signals that reflect the fluctuations in the number of activated neurons or the alternating component of the mean soma potential over time. The first derivative of EEG signal has been shown to be strongly linked to the mean soma potential based on Cellular Automaton (CA) simulations of cortical function. The step of computing the first or second derivative of the signal is performed on a processor, in real time, and substantially at the same time as the signal is being acquired. Substantially at the same time means that immediately as the signal is acquired by the circuitry and apparatus described above, the processor computes the appropriate derivative of that signal.

In various embodiments of the present invention, the acquired EEG signal may or may not be filtered prior to computing the first (or higher) derivative and analyzing the signal. In those embodiments which require signal filtering, such filtering is performed by means of a low-pass filter used to remove high frequency (HF) interference from the EEG signal. Examples of HF interference that may need to be filtered out of the EEG signal include other physiological signals such as electromyographic (EMG) signals, as well as outside HF interference such as background electrical noise and noise from electro-surgical units (ESUs). Preferably, when filtering is performed, the low-pass filter is set to allow EEG signals with a frequency of 32 Hz and less to pass. More preferably, the filter allows EEG signals with a frequency of 30 Hz and less to pass. More preferably still, the low-pass filter allows EEG signals with a frequency of 24 Hz and less to pass. Even more preferably, the low-pass filter allows EEG signals with a frequency of 16 Hz and less to pass.

Another step in various embodiments involves analyzing an epoch of predetermined size of the first derivative of the EEG signal using at least one suppression detection parameter, the at least one suppression detection parameter being used to detect suppression in the EEG signal. The suppression detection measure can be virtually any type of operator or algorithm which is capable of detecting the drastic changes in the EEG signal which may be representative of burst and suppression periods. Such suppression detection measures may include, but are not limited to the median absolute value, the peak-to-peak time measurement, root mean square (RMS), spectral measures, entropy measures, energy operators, and the like. Preferably, at least one suppression detection measure used is the median absolute value of the first derivative of the EEG signal. The median absolute value is a robust measure of the rate of change of EEG, is less sensitive to outliers, and corresponds with the visual recognition rules of suppression detection. Thus, as the EEG, or other physiological signal, is acquired, the processor first calculates the first derivative of that signal, and essentially simultaneously computes at least the median absolute value of that first derivative signal.

Still another step in various embodiments of the present invention involves utilizing the above calculated suppression detection measure (i.e., median absolute value) for the detection of suppression periods in the EEG signal. If the above calculated suppression detection measure (i.e., median absolute value) is below a predetermined threshold for a predetermined amount of time, then that particular epoch is determined to be suppression.

Some embodiments include a step in which the suppression periods are confirmed by the existence of burst periods in the last minute to ensure that low-amplitude EEG activity is not detected as suppression, while still making sure that slight EEG activity during suppression periods between the bursts doesn't preclude the detection of suppression. If the above calculated suppression detection measure (i.e., median absolute value) is above another predetermined threshold for a predetermined amount of time, then that particular epoch is determined to be burst. Preferably, the suppression periods are confirmed based on at least 10 seconds of burst in the last minute. More preferably, the suppression periods are confirmed based on at least 5 seconds of burst in the last minute. More preferably still, the suppression periods are confirmed based on at least 3 seconds of burst in the last minute. Even more preferably, the suppression periods are confirmed based on at least 1 second of burst in the last minute. More preferably yet, the suppression periods are confirmed based on at least 0.5 seconds of burst in the last minute. Even more preferably still, the suppression periods are confirmed based on at least 0.25 seconds of burst in the last minute.

Some embodiments include a step in which artifacts are detected and identified, and are not counted as periods of burst activity. These artifacts may be those that were not detected by the front-end filtering, or new additional artifacts that corrupt the signal after initial filtering. In this optional step, the present invention differentiates between such artifacts and burst activity. This means that the system does not count an aberrant artifact as burst activity and thus effect the detection of burst and suppression periods and their durations. This is another step to increase the accuracy of the invention in environments that create artifacts in the EEG signal.

Some embodiments of the present invention further include a step by which the thresholds used for detecting a burst or suppression period are automatically relaxed or tightened based on environmental factors. For example, if the signal contains a particularly strong or high amplitude period of burst activity, the threshold may be relaxed so the results of the detection methods are not artificially skewed or misidentified.

Still further embodiments of the present invention may involve using the second-derivative of the EEG signal to perform the suppression detection methods. In such embodiments, similar methods may applied wherein suppression detection measures such as the median absolute value, mean, median, RMS, peak to peak, spectral measures, entropy measures, energy operators, or the like are used to calculate their respective values, and those values compared against appropriate thresholds to determine whether suppression or detection is occurring.

Still another step in various embodiments of the present invention involves outputting a signal, preferably through some variety of output devices or combination of devices capable of providing an alarm or signal, where the signal is based at least in part on the occurrence of suppression in the EEG signal to a device for communicating the outputted signal to a clinician monitoring the patient. The output device may be a visual alarm or signal display such as a monitor or lights, an audio device such as a speaker or audio message, a tactile output device such as a vibrational motor (similar to a cellular phone vibration ring notification), or a combination thereof. This output signal may be any form of signal designed to get the clinician's attention and alert her to the fact that suppression has recently or is presently occurred. Preferably, the output signal is the percentage of suppression detected in the EEG signal during the last minute, known as suppression ratio (SR). It may also include audio warnings or alarms, or visual indicators on a monitor such as a text warning, flashing windows, colors, and the like, or any combination thereof.

Other embodiments may include the step of outputting a signal based at least in part on the occurrence of suppression in the EEG signal to a device for controlling the patient's level of anesthesia and amount of suppression. In this step, rather than, or more preferably in addition to alerting a clinician to the occurrence of suppression in a subject under anesthesia, the subject is instead attached to a closed-loop, or semi-closed-loop drug delivery device which automatically controls the amount of sedative or anesthetic being administered to the subject.

Some embodiments may utilize a bilateral monitoring method to measure EEG signals from the two hemispheres (left and right) of a subject's brain independently and simultaneously. In such embodiments, at least three electrodes (or sensors) are utilized, one measurement EEG electrode to measure EEG signals of the left hemisphere, one measurement EEG electrode to measure the EEG signals of the right hemisphere, and one reference electrode. Such embodiments, preferably, the physiological electrodes or other sensors are placed on the subject's head with at least one measurement electrode on each side of the subject's head (i.e. left and right sides as divided by the sagittal physiological plane). Also preferably, at least one reference electrode needs to be placed in order to obtain and measure the differential EEG signals from each of the measurement electrodes. In order to be able to compare the signals from the left and right hemispheres of the subject's brain, the reference electrode is preferably placed as close as possible to the center of the subject's head. This placement should coincide with the location of the longitudinal fissure. When placed as close to the longitudinal fissure as possible, the reference electrode will receive EEG signals from both hemispheres of the subject's brain, and therefore produces a common signal that can be used to create accurate and comparable differential calculations between the EEG signals measured from each individual brain hemisphere. This process is described in greater detail in U.S. Patent Application Publication No. 2011/0130675 A1, which is incorporated by reference.

Many embodiments of the present invention include brain function monitoring algorithms. The brain function monitoring algorithms use the acquired EEG signals, and process them specifically to determine the subject's brain state, presence and/or level of injury (e.g., TBI) or other abnormal function (e.g., seizure). Examples of some algorithms that may be utilized for brain dysfunction detection are included in U.S. patent application Ser. No. 12/259,652, and U.S. patent application Ser. No. 13/731,315, which are herein incorporated by reference, though other similar algorithms known to those skilled in the art may be used as well. In many embodiments, the same or other algorithms may include the means to determine the level of cortical activity of the subject in order to automatically adjust and control the delivery of drugs to maintain a desired or predetermined level of sedation, or a desired or predetermined depth of anesthesia.

In many embodiments of the present invention, the display device may be substituted for an Integrated Monitoring and Infusion System (IMIS). The IMIS comprises many of the above components in order to perform signal acquisition, pre-processing, analysis, make status determinations, monitor a subject's brain function, and to display various signals and/or indicators. In other words, the IMIS essentially comprises all of the display device functions and features, but also incorporates several additional components, features, and capabilities to perform additional functions of determining a desired or predetermined level of cortical activity, monitoring the subject's cortical activity level, and automatically adjusting the delivery of sedative, anesthetic, and/or analgesic drugs to maintain that desired or predetermined level of cortical activity. Such system can also be used to drive a patient to a new cortical activity target that is more adequate for the clinical situation.

The IMIS embeds one or more control algorithms into a control module, which allows for closed-loop operation; however, in case of adverse conditions, partial or total system failures, or other system errors, the closed-loop function may be overridden and the system controlled manually by the caregiver. By closed-loop, it is intended that the system operate automatically, continuously, and without human interaction once the system has been applied to a subject and set into motion. The control module is designed to regulate the infusion rates of an intravenous hypnotic (sedation or anesthetic) and optionally also an opioid (analgesic) drug. In a preferred embodiment, both a hypnotic and an analgesic drug are administered by individual infusion pumps (described below). The administration of both drugs is typically required to provide a state of balanced anesthesia to the subject, where the subject neither perceives nor recalls noxious stimulation. A controller is used to govern the administration of the anesthetic or sedative medication(s) or drug(s). The controller uses various forms of inputs, such as programs or commands from a user (e.g., label indications based on drug manufacturer recommendations, patient demographics, and the like) and/or measured values from the system (e.g., EEG, EKG or other signals), and adjusts the administration of the anesthetic or sedative based on those inputs. Basing controller and pump operation on the manufacturer recommendations allows the system to ensure that the particular anesthetic or sedative is used according to properly tested guidelines and that the system cannot exceed the recommended maximum values indicated. The controller uses a measurement of the cortical activity of the subject. This measurement can be based on spectral or bispectral analyses, or preferably using wavelet analysis, or any of the other measurements described above, either individually, or in combinations thereof. Ideally, an index of cortical activity used in a closed-loop application should introduce no delay and be linear and time-invariant (LTI) across its whole operating range.

One such EEG index that complies with these requirements is the $WAV_{CNS}$ index, developed by some of the applicants. The $WAV_{CNS}$ index quantifies the effects of anesthesia drugs on the brain using wavelet analysis of frontal EEG signals. It is expressed in a 100-0 scale where "100" represents the awake conscious state and "0" represents the total suppression of cortical activity. A suitable state for performing surgical procedures (i.e., general anesthesia) is between 40 and 60, while a sedated subject is between 60 and 80. A conscious subject produces a value well above 80, while subjects induced into deep coma (e.g., for stroke surgery or refractory seizure control) would have $WAV_{CNS}$ values below 10. Wavelet analysis is a powerful signal processing technique particularly well suited for non-stationary EEG signals. The wavelets are able to simultaneously and rapidly characterize changes in both time and frequency, which more traditional spectral analyses are typically unable to track timely. The $WAV_{CNS}$ rapidly captures fast changes in cortical activity. Another particularly important advantage of the $WAV_{CNS}$ quantifier lies in its consistent and well-defined transient behavior during patient state changes. The only dynamic difference between the physiological effect and its quantification through the $WAV_{CNS}$ algorithm is due to the post-analysis trending filter, which is well-defined, linear and time-invariant. Preferably, feedback quantities used for regulation (i.e., in closed-loop systems) should be LTI to ensure that their input-versus-output relationship can be accounted for by the controller, and that they do not add uncertainty. An ideal sensor for control should not introduce non-linearities (especially discontinuities) and should not introduce (unknown and variable) additional delay. From a control perspective, cortical activity sensors that are LTI represent the best-case scenario. Non-LTI sensors, on the other hand, introduce uncertainty in the system, which leads to instability if not properly accounted for, and/or a reduction in the controller performance. A non-LTI brain function monitor used in a closed-loop application could result in an inaccurate and/or delayed EEG interpretation during sudden changes in cortical activity (due to, e.g., a sudden change in drug administration or change in surgical stimulation). Consequently, in embodiments performing automated sedation control, the overall regulation of anesthetic delivery would be more prone to instability and therefore less safe. The existence of a reliable mathematical function relating a physiological change in drug effect and its corresponding quantification by the $WAV_{CNS}$ means that the effect of the monitoring technology can be fully accounted for in the controller. In addition, it is important that the cortical activity sensing technology does not introduce additional uncertainty in the system, which will ultimately provide better closed-loop performances. Though the $WAV_{CNS}$ index is preferred, other indexes or indices describing a subject's brain or cortical activity can be envisioned and used in conjunction with the present invention, for example the BIS index.

While a single measure can be used, it may be preferable to use a bilateral measure of the cortical activity in order to provide redundancy in the system. In healthy individuals, the left and right hemisphere measures should be equivalent, e.g., in terms of $WAV_{CNS}$, to within a defined degree or threshold. The caregiver could then set the system to operate based on the right hemisphere measure, or the left hemisphere measure, individually. Preferably, the system uses both measures, and outputs a warning to the caregiver and/or automatically adjusts the infusion of hypnotic and/or sedation drugs (in some embodiments) when both measures are significantly different. Preferably, such warnings and/or automatic control are triggered when the difference between the left and right hemisphere measures is greater than 5 percent. More preferably, the warning and/or controls are triggered when the difference is greater than 10 percent. Still more preferably, the warning and/or controls are triggered when the difference is greater than 12 percent. Even more preferably, the warning and/or controls are triggered when the difference is greater than 15 percent. Even still more preferably, the warning and/or controls are triggered when the difference is greater than 20 percent. Such significant difference could be the result of heavy artifact activity in one channel, or an existing or developing neuro-pathology. Alternatively, the control module may continuously assess the quality of the EEG signals from both channels, and automatically use the best channel for its feedback measure. Alternatively, in other embodiments, the system may average both measures in order to further limit the measurement noise.

The control module then calculates the difference between a predetermined set point defined by the caregiver or pre-programmed into the system, and the feedback measure. A control algorithm will then calculate an adequate modification of the infusion rates of either one or both drugs, either using a standard proportional-integrative-derivative (PID) control structure, or a more complex control structure based on robust control methods to guarantee stability in view of subject variability. A standard PID is a control loop feedback system that calculates an "error" value as the difference between a measured variable and a desired or predetermined set point using at least three constant parameters: proportional error value, integral error value, and derivative error value. These three parameters are then weighted and summed and that sum is used to automatically adjust the infusion rates to minimize the error value.

In a preferred embodiment, a robust controller is specifically tuned to remain stable in view of a certain degree of variability. In some instances, the expected amount of subject variability for which the controller needs to account can be reduced by providing or inputting some subject-specific information to the system, such as the subject's age, weight, height, gender, ethnicity, etc. via an input or interface device or component. Based on this information, the robust controller can be more aggressive.

In one instance, a robust PID controller can be designed to effectively account for patient variability in such a way that a unique controller can be used for a wide population of patients. Patient variability is probably the most challenging aspect in "closing the loop." Quantifying this variability and expressing it as a system uncertainty is a first step in order to prove the stability of the controller when closing the loop. Once a robust design is achieved, performance can be assessed to verify that it meets clinical expectations. Methods and systems for quantifying patient variability are taught in U.S. patent application Ser. No. 13/962,565, to which the present application claims priority as a continuation-in-part, and which is incorporated herein by reference in its entirety.

An important safety aspect is also to limit the control action of the controller. For instance, the caregiver can define upper and lower infusion rates that the controller cannot exceed without the caregiver's acknowledgement. Preferably, the caregiver could define upper and lower effect-site or plasma concentrations beyond which the controller should not operate. In this case, the controller would not be able to derive an infusion profile which would lead to a violation of these upper and lower concentration bounds. The effect-site or plasma concentration may be either estimated using pharmacokinetic and/or pharmacodynamic models, or directly measured through blood analysis or other biomarkers. Alternatively, these limits may be predetermined and preprogrammed into the system.

In a preferred embodiment, the safety limits are directly calculated based on the drug manufacturer's recommendation, or label indications as provided with the medication. These recommendations are typically based on the patient's weight, age, height, gender and overall health status. By entering this information in the system, the user will be proposed a de facto minimum and/or maximum infusion rate, or drug dosage that the system will not exceed. These pre-calculated safety limits may be overridden by the user at any time.

The control module should preferably take as input the effective infusion rate delivered by the infusion pump(s), and not the rate determined by the controller. The effective rate is either measured by the pump, using appropriate sensors, or is simply the rate at which the pump currently operates. The effective rate may be different than the rate the controller outputs. Preferably, the closed-loop system should not assume the rate it has sent the infusion pump is equal to the effective rate. In case a syringe is empty, or if the caregiver may stop the pump manually, the controller may compensate for the lack of drug injected to the subject by catching up once the pump is operational again. This is typically done through the predictive part of the control algorithm. For safety reasons, any issue with the infusion pump(s), such as an empty syringe, a line occlusion, loss of communication/power, etc., should be systematically delivered to the caregiver. Such delivery can take place via audio signal, visual signal on the display, wireless communication, or the like. Another safety issue is to validate that each pump is delivering the right drug. This can be done by prompting the caregiver to validate the drug and drug concentration prior to starting the case.

Another useful feature of the control module is its ability to detect out-of-the-ordinary subjects, e.g., subjects which may require much higher or much lower drug administration. Such subjects may be suffering from an underlying pathology, for example. The control module could automatically and continuously measure the difference between the amount of drug effectively administered, and the amount of drug that would have been administered in open-loop, i.e., based on a pharmacokinetic and pharmacodynamic model of the subject. If there is a large difference between the two, the subject differs significantly from the norm. This information may be useful to the caregiver, as it may denote an abnormal volemia, or metabolism.

As noted above, many embodiments of the present invention further comprise at least one drug infusion device. The drug infusion devices envisioned for use with these embodiments may be of a typical syringe infusion pump presently known to those of skill in the art. Such infusion pumps will be particularly suited for embodiments wherein the IMIS is integrated into a medical transport or evacuation vehicle, and thus wherein the IMIS may be a larger system that is mounted in a stationary manner within said vehicle. However, many other embodiments will utilize a miniaturized, portable infusion pump(s) in order to provide sedation control and/or pain control in the field until such medical transport can arrive, or the subject can be delivered to a higher echelon of medical care.

In the envisioned syringe infusion pumps, a piston applies pressure on a disposable syringe filled with the drug to be delivered, either a hypnotic (sedative or anesthetic), or analgesic drug. Infusion pumps can allow for very small rates of delivery (i.e., less than 0.1 milliliters per hour) or larger rates of delivery (i.e., more than 1,000 milliliters per hour), which makes them ideal for delivering either rapid boluses or much slower and longer infusions. The infusion pump mechanism itself is preferably very simple and is constructed of a light frame of metal (e.g., aluminum) or plastic, where a cursor moves up and down along a screw whose angular position and rotational speed is controlled through a gear connected to a brushless stepper motor. The cursor is attached to the syringe plunger such that pressure on the plunger can be exerted when the stepper motor rotates. When such pressure is placed on the syringe plunger, it slowly forces the plunger through the syringe, thus dispensing the particular drug out of the needle end of the syringe.

Although syringe pumps are envisioned for most embodiments, in some embodiments other types of pumps may be used. Peristaltic pumps provide the advantage of permitting a very large reservoir, and may be used when it is anticipated that a large quantity of drug may need to be delivered over an extended period of time. Other embodiments may utilize a reservoir with a specific, pre-determined volume of drug or medication to be delivered to a subject. For example, a small reservoir containing several doses, enough for medical transportation to a stationary care environment, may be used in certain embodiments rather than a large-volume reservoir for continued use over a period of time. Volumetric pumps, gravity-based pumps, or any other type of pump known to those skilled in the art might also be used. Drug delivery may also be performed by providing a vaporized, atomized or gaseous drug which is inhaled by the patient or subject to induce anesthesia or sedation. In such case, the delivery of the drug may be made by means of an oral or oral-nasal mask, a nasal cannula, or other suitable means, and the IMIS would include, as appropriate, a pressurized canister for the gaseous drug, or a vaporizer or atomizer. The closed-loop delivery system would then control a pressure valve or other flow control apparatus, instead of (or in addition to) a syringe pump or similar pump, in order to regulate the delivery of the drug to the patient or subject. In such oral or oral-nasal delivery embodiments, the entire system may be integrated as a face mask that secures to the head with an elastic band or strap, or other suitable attachment methodology or apparatus that simultaneously ensures the appropriate EEG sensor connections on the forehead and/or temples and securely seals the delivery system around the airway entrance(s). Preferably, in such embodiments, the entire system is integrated into the face mask, providing for ease of application and use in a battlefield or other emergency scenario to provide fast and easy administration of closed-loop sedation or anesthesia.

In many embodiments, the particular type or variety of drug delivery pump(s) chosen may be directly influenced by the type of drug being administered. Thus, it may be preferable for the system to be modular in nature such that several types of drug infusion pumps may be used simply by attaching the different pump to a base unit. Also preferably, the system is designed to work with and administer a large variety of types of drugs to a subject. One particular class of drugs the systems, devices and methods of the present invention are designed to administer includes vapor or inhaled sedatives and anesthetics, which includes drugs such as, for example, sevoflurane, isoflurene, desflurane, and other like drugs. Another class of drugs the systems, devices and methods of the present invention are designed to administer includes intravenous sedatives and anesthetics, which includes drugs such as, for example, barbiturates, benzodiazepines, phencyclidine, carboxylated imidazole, isopropylphenol, dexmedetomidine, and other like drugs. Still another class of drugs the systems, devices and methods of the present invention are designed to administer includes opioids, which includes drugs such as, for example, morphine, fentanyl, alfentanil, sufentanil, remifentanil, and other like drugs.

In practice, infusion pumps for human use must be certified to have no single point of failure. That is, no single cause of failure should cause the pump to silently fail to operate correctly. The infusion pump should at least stop pumping and make at least an audible error indication. This is a minimum requirement on all human-rated infusion pumps. At a minimum, the angular velocity of the motor drive and the cursor position must be measured in real-time to verify that they both correspond to the expected infusion rate set by the IMIS. Any difference between the two measures automatically shuts down the power to the drive and outputs a visual and/or audible alarm.

The infusion pump(s) of the present invention further comprise additional sensors and features that are required for use of such infusion pumps on humans: (1) an anti-free-flow device to prevent blood from draining from the human subject, or prevent the drug from freely entering the human subject, when the infusion pump is being set up; (2) a pressure sensor to detect occlusion (e.g., vein blockage, or kink in the line); and (3) a syringe lock mechanism to verify that the syringe is properly placed and to check its outer diameter. In addition, the IMIS system may also be capable of battery operation so that drugs can be infused to patients during power failure. The IMIS will also keep a detailed log of the pump operation, including start and end time of infusion, infusion rates, total volume administered, etc. This detailed log will be stored along with other data, as described above, on the internal removable or non-removable memory. Alternatively, or in conjunction with the internal memory of the system, the IMIS will be capable of maintaining a very large database using a large capacity solid-state drive.

It should be noted that, while the IMIS depicted in FIGS. 6A-6J integrates the infusion mechanism for ease-of-use and limit size and weight, other embodiments exist where the IMIS controls external infusion systems via, for example, a parallel or serial bus interface (e.g., USB, RS232, or the like), a network interface (TCP/IP protocol), or via a wireless interface (e.g., Wi-Fi, Bluetooth, or the like).

Figure 8:
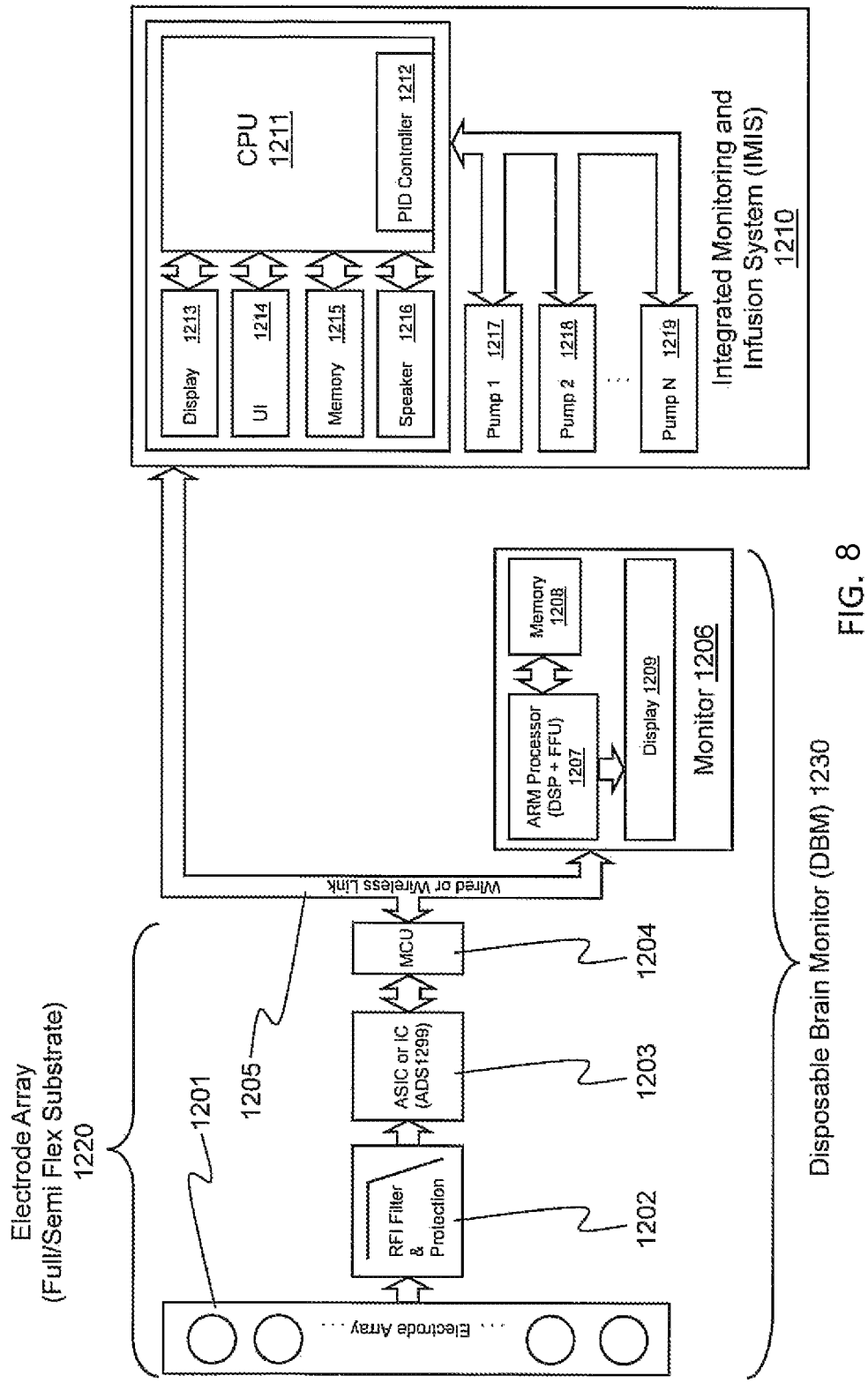
FIG. 8. Electrode/display integrated block diagram showing the arrangement of components in the physiological signal monitor and IMIS.

In most embodiments, the IMIS embeds a graphical user interface (GUI), such as the one depicted in FIG. 8. The user interface, at a minimum, displays one or more EEG signals that are used to make the cortical activity level determination. The interface also displays the real-time cortical activity level and its time course over time. A panel gives the user the ability of turning on or off the closed-loop feature, or to manually change the infusion rate. An emergency stop button allows the user to stop the infusion. Conversely, a bolus button allows the user to deliver a large amount of drugs in a short amount of time, e.g., to induce a patient into an anesthetic depth. An indicator on the cortical activity level time course shows the range of cortical activity level targeted by the system. Optionally, other graphs showing the estimated plasma and effect-site concentrations can be displayed to aid in the manual operation of the system. Also optionally, a future predicted time course of the plasma and effect-site concentrations, and/or effect can be displayed based on pre-programmed models. The future predicted time course can be useful to determine, for example, how long it will take to bring a patient into a lighter or deeper cortical activity level range, or to determine how long the closed-loop controller will take to bring the patient into the targeted zone. Another useful feature of the GUI is the creation of a data log. With each case, a data archive should be created containing at the very least the time course of the feedback variable (e.g., the $WAV_{CNS}$ index) as well as the controller outputs and the infusion pump rates. In some embodiments, the data log should also contain the user actions on the system, as well as a list of all the alarms and warnings during the case. The data log can be used for data audit purposes, or to serve as basis in future improvement of the system.

In a preferred embodiment, the GUI should be developed in such a way to minimize user confusion and user error while ensuring that the user verifies all the proper settings on the pump(s) and of the closed-loop system. A confirmation based GUI can be envisioned, where the user is asked to confirm his/her choices before being allowed to move to the next stage. Once all the confirmations have been obtained, the system allows the user to "close the loop."

The closed-loop feature of the IMIS is particularly useful in patients for whom the administration of total intravenous anesthesia (TIVA) is difficult or complicated by existing co-morbidities, in particular, for patients suffering from hepatic/renal failure, hemodynamic instability, or hypovolemia.

Although the illustrations show a GUI integrated into the IMIS, the IMIS in some embodiments may be controlled by a separate display/interface device, such as a smartphone, tablet computer, portable computer, medical grade computer monitor, or other similar device, which is connected to the IMIS by wired or wireless connection.

Preferably, the IMIS calculates the drugs minimum and maximum dosage as recommended by the drug manufacturer, based on the weight of the patient or subject, and/or other parameters as discussed herein or as would be known to a person skilled in the art. These one or more parameters may be entered by the user or responder prior to the administration of drug to the patient or subject through the GUI. The GUI preferably asks the user or responder to confirm entered parameters prior to administration of drug to the patient or subject, and provides for sensible error-checking to prevent entry of unlikely parameter values or combinations of parameter values. For example, an entry of 2,000 pounds for human subject weight is likely to be the result of a miss-entry, such as one too many zeroes input for the weight value. The user of the system may override the minimum and maximum dosages at any time. Preferably, the device is configured so as to make it impossible to administer the drug outside of either the drug manufacturer recommended dosages or outside the dosing limits specified by the user. As such, the IMIS provides for safety and risk mitigation.

Given that the system is designed to keep the subject in a preferred range of anesthetic or sedative depth, it is important to consider what occurs when the subject goes too deep into anesthesia or sedation. Such occurrence is referred to as suppression, or burst suppression. Suppression, particularly of EEG activity, is indicative of anesthesia or sedation that is so deep as to effectively stop brain function. Such condition might be desirable, for example where the subject is placed into a medically induced coma. However, for patients where such a level of anesthesia or sedation is not desired or predetermined, suppression can lead to injury and long-lasting harmful effects to the patient. Thus, many embodiments of the present invention further include the ability for the system to detect burst suppression, to automatically cease or reduce operation of the infusion pumps to stop administration of additional anesthetic or sedative medication or drug, and to alert or otherwise signal a clinician to notify that suppression has been detected in order for the clinician to tend to the patient and mitigate any harmful effects of the suppression. Effectively, the physiological signal monitor acquires the physiological signal and the processor analyzes the signal, preferably in real-time, at least partially attempting to detect burst suppression. When burst-suppression is detected, the processor sends a signal to the controller instructing the controller to cease or reduce administration of the anesthetic or sedative by stopping or ceasing operation of the infusion pump. In some embodiments, the system may also cease or reduce operation of the infusion pump when one of the programmed label indications for the particular drug or medication is reached. For example, if the system detects that the maximum recommended dose volume has been reached, then the pump would be stopped and no additional drug or medication will be administered until an appropriate amount of time has passed so as to allow for another dose, or if a clinician overrides or changes the settings of the system. Additionally, in many embodiments, the system further provides an alarm or some other signal to a clinician indicating that suppression has been detected and that the subject needs immediate attention to mitigate the suppression of the physiological signal.

For these embodiments where the system is designed to cease or reduce administration of the drug(s) or medication (s) in response to detection of some adverse condition, such as burst suppression, the process for resuming normal function of the system to provide further anesthesia or sedation may vary based on whether the system is fully closed-loop or semi-closed or open-loop, or based on whether the embodiment calls for multiple layers of safety before resuming function. One method of resuming operation of the system is to require the clinician to manually reset or instruct the system to be able to increase or resume administration of the anesthetic or sedative. This method is likely necessary for semi-closed and open-loop systems, but may be optional for a normally fully closed-loop system. Once the system detects an adverse condition, such as burst suppression, and ceases or reduces administration of the drug(s), the alarm notifies the clinician of the condition, and the clinician must respond to halt the alarm or signal and tend to the subject. Once the subject has been checked as in safe condition, the clinician must then manually instruct the system to increase or resume administration of the drug. Without direct instruction from the clinician, the system will remain in an off or standby mode and not administer any further drug or medication. This ensures that only when the clinician specifically verifies that the subject is stable and not in further danger of harm or injury that the system can resume providing anesthesia or sedation to the subject. The manner in which the clinician interacts with the system to instruct it to resume depends on the specific embodiment, and may be done locally by direct interaction the interface or controls of the system, or may be done remotely by way of remote communication with the system from a separate console or device. Fully open-loop systems, in some circumstances, may require clinician instruction to resume or restart, such as if the adverse condition (i.e., burst suppression) is prolonged for a given period of time, if the alarm or signal goes unanswered for too long, or if the adverse condition is detected to be particularly severe, or the like. Such circumstances would dictate, even to a fully closed-loop system that the subject's condition is so dangerous that clinician involvement is necessary to prevent severe harm to the subject. This may effectively render such a system a semi-closed loop system in such instance, but generally the system may operate in a fully closed-loop mode unless extenuating circumstances arise. In normal full closed-loop operation, the system may automatically increase or resume administration of drug(s) or medication(s) after detection of an adverse condition and ceasing of operation. Generally, such embodiments would allow the system to automatically restart if the adverse condition is no longer detected, is particularly mild or non-severe, and/or if other conditions are met that dictate that direct clinician interaction is not entirely or immediately required. The physiological signal monitor and processor would determine that the adverse condition no longer exists, and the processor would then send a signal to the controller to resume function of the infusion pump to continue administering the drug or medication to the subject.

Figure 1B:
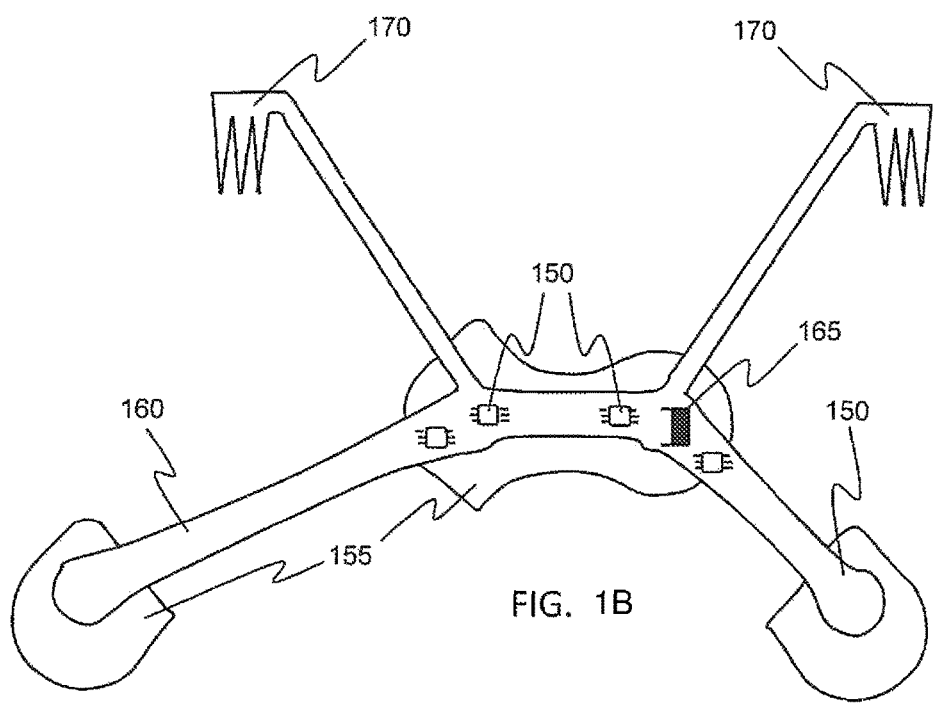
FIG. 1B. Depiction of another embodiment of the flexible substrate with electrode array, this one having semi-rigid comb structures used to help attach the electrode array to the subject's head in the presence of hair.
Figure 2A:
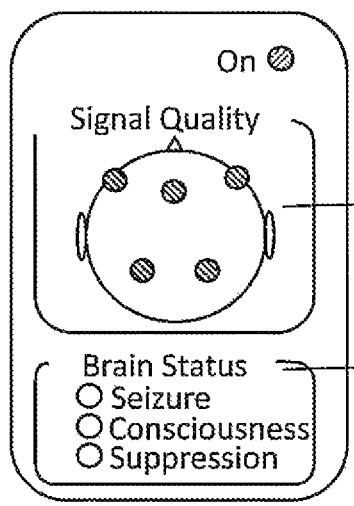
FIG. 2A. Depiction of an embodiment of the display portraying electrode signal quality and injured subject's brain activity with respect to potential presence or absence of seizure, consciousness or suppression.
Figure 2B:
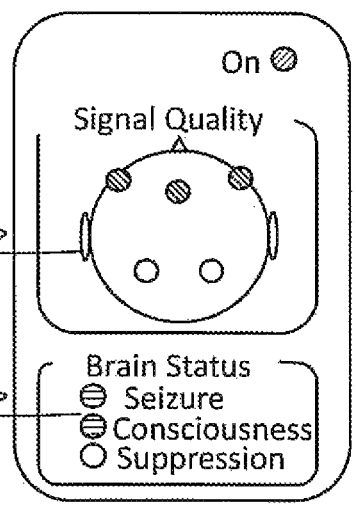
FIG. 2B. Depiction of an embodiment of the display portraying electrode signal quality and injured subject's brain activity with respect to potential presence or absence of seizure, consciousness or suppression.
Figure 2C:
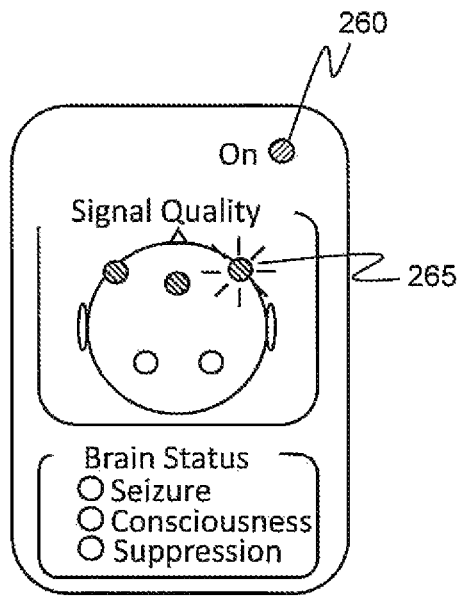
FIG. 2C. Depiction of an embodiment of the display portraying electrode signal quality and injured subject's brain activity with respect to potential presence or absence of seizure, consciousness or suppression.
Figure 2D:
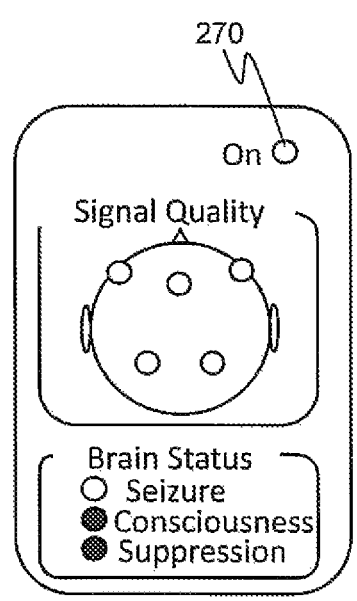
FIG. 2D. Depiction of an embodiment of the display portraying electrode signal quality and injured subject's brain activity with respect to potential presence or absence of seizure, consciousness or suppression.

FIGS. 1A and 1B depict two embodiments of the electrode array. FIG. 1A shows a flexible substrate 160 into which the electrodes (not shown) are embedded or otherwise affixed. The electrodes (not shown) are applied to the subject's (not shown) head and held down securely by adhesive pads 155. Aside from the electrodes, the flexible substrate 160 has embedded ASIC chips or other suitable ICs which comprise the amplification, filtering, and analog-to-digital conversion (signal pre-processing) electronics. Miniaturizing and embedding these ASIC chips or other suitable ICs into the flexible substrate serves to make the device a more integrated, portable, easy to apply device by removing the need for a separate processor to carry out these functions. Further, a connector 165 is provided which allows for the portable, in some embodiments disposable display unit (not shown) to be easily and quickly attached and detached from the electrode array. In FIG. 1B, all of the same features as in the FIG. 1A embodiment are present, with the addition of one or more semi-rigid comb structures 170 which are used to help attach the electrode array to the subject's head in the presence of hair. These comb structures 170 are particularly useful for attaching electrodes for occipital and parietal channel monitoring. The geometry of the comb structures illustrated is intended only to be exemplary of a comb and not a preferred geometry. A person skilled in the art would appreciate that different comb tooth shapes and lengths would be more useful depending on the type and thickness of hair, and that optimal comb tooth shapes and lengths could be arrived at through routine experimentation.

FIGS. 2A through 2D depict an alternate display embodiment whereby signal quality and brain status are displayed simultaneously. Signal quality 250, which may provide a graphical display of the head of the subject or patient and thereby show the electrodes by their relative positions thereon, indicates the electrical impedance of the electrodes. When the electrical impedance of any of the electrodes becomes too high, indicating an issue with the electrode itself or the connection between the electrode and the subject's scalp, and indicator or light 265 alerts the responder or user that the signal quality is poor in that electrode. This alert allows the user or responder an opportunity to replace the electrode or reaffirm its connection. The indicator or light may perform its function by changing color (e.g., from green to yellow, orange, or red, or some sequence thereof as impedance progressively worsens), by blinking (e.g., by blinking progressively faster or more slowly as impedance worsens), by deactivating or de-lighting, or by any other means known in the art to attract the attention of the user. Such indicator or light preferably accompanied by an alert tone, bell or alarm issued from a loudspeaker (not shown) that is optionally provided within the display.

Additionally, the subject's brain status 255 is displayed. In the particular embodiment shown, lights or indicators are given for three different brain conditions: seizure, consciousness, and suppression, though others may additionally or alternatively be included. If any of these conditions are detected in the subject, the light or indicator alerts the responder or user. In some embodiments, the indication of one of these conditions might trigger an attached or integrated IMIS (not shown) to supply some drug in order to counteract the brain status. Additionally, an indicator 260 is provided to give notice of the status of the brain monitor itself. If the light is on (or a particular color, for example green, or in some other way is a positive indicator), that means the device is properly connected to the electrode array and that the device is adequately powered. If the light is off 270 (or has turned another particular color, for example red, or in some other way indicates negatively), then either the device has run out of power, or the electrode array is not connected, and thus the display indicates that no monitoring is taking place. A blinking light 270 (or indicator that progressively changes color from, for example, green to yellow to orange to red) may indicate failing battery power and thus provide warning that the system will cease operation soon.

Figure 3:
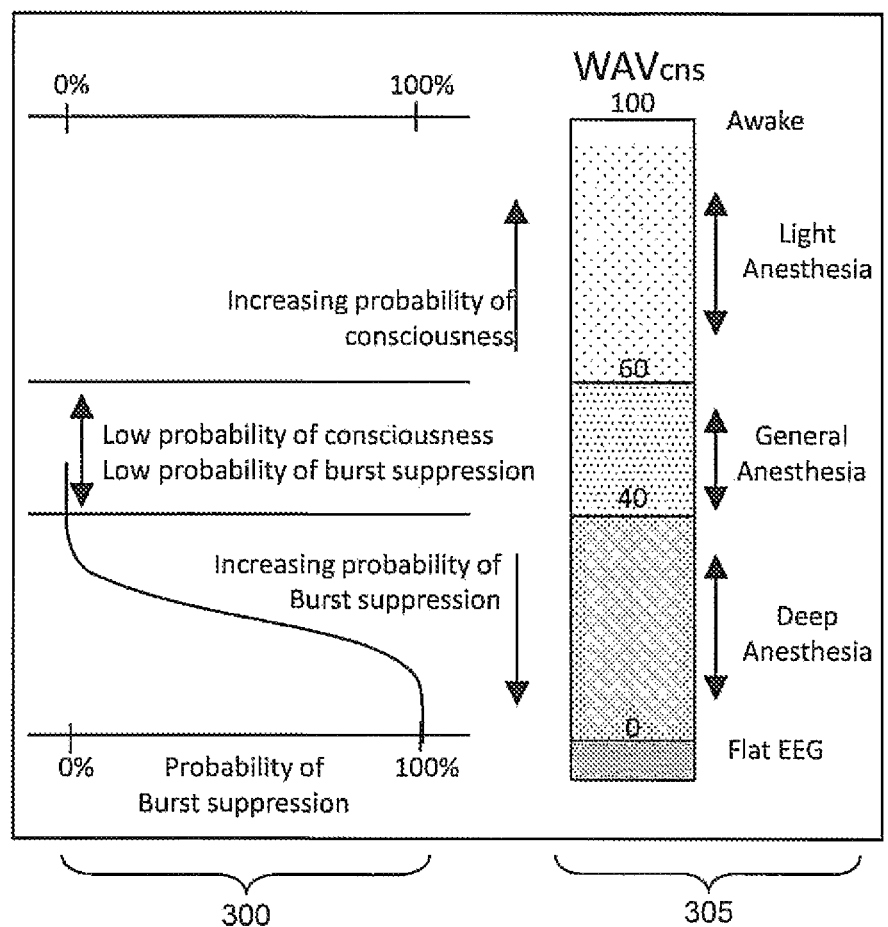
FIG. 3. Graph showing the correlation between the $WAV_{CNS}$ index (an indicator of consciousness used by the present invention) and subject consciousness or level of sedation or anesthesia.

FIG. 3 depicts the $WAV_{CNS}$ scale of the present invention, and provides a comparison of the particular $WAV_{CNS}$ index 305 numbers to the corresponding likelihood 300 of the subject being in a particular brain state. The $WAV_{CNS}$ scale represents the degree of cortical depression achieved through the administration of central nervous system (CNS) depressant drugs, such as sedatives or anesthetics. As the drug effect increases, the $WAV_{CNS}$ index decreases. When the $WAV_{CNS}$ index is at or near 100, it means the subject is very likely fully awake or conscious. As the drug begins to take effect, the patient enters a state of light anesthesia or sedation, and the $WAV_{CNS}$ index drops while the likelihood of the subject being fully conscious decreases. As the subject enters a level of general anesthesia or sedation, corresponding to a $WAV_{CNS}$ index of between 60 and 40, the subject has a very low probability of being conscious, but also a very low probability of burst suppression. However, if the drug effect continues to strengthen, the $WAV_{CNS}$ index drops further (e.g., below 40) and the subject enters deep anesthesia or sedation, and the likelihood of burst suppression activity increases.

Figure 4:
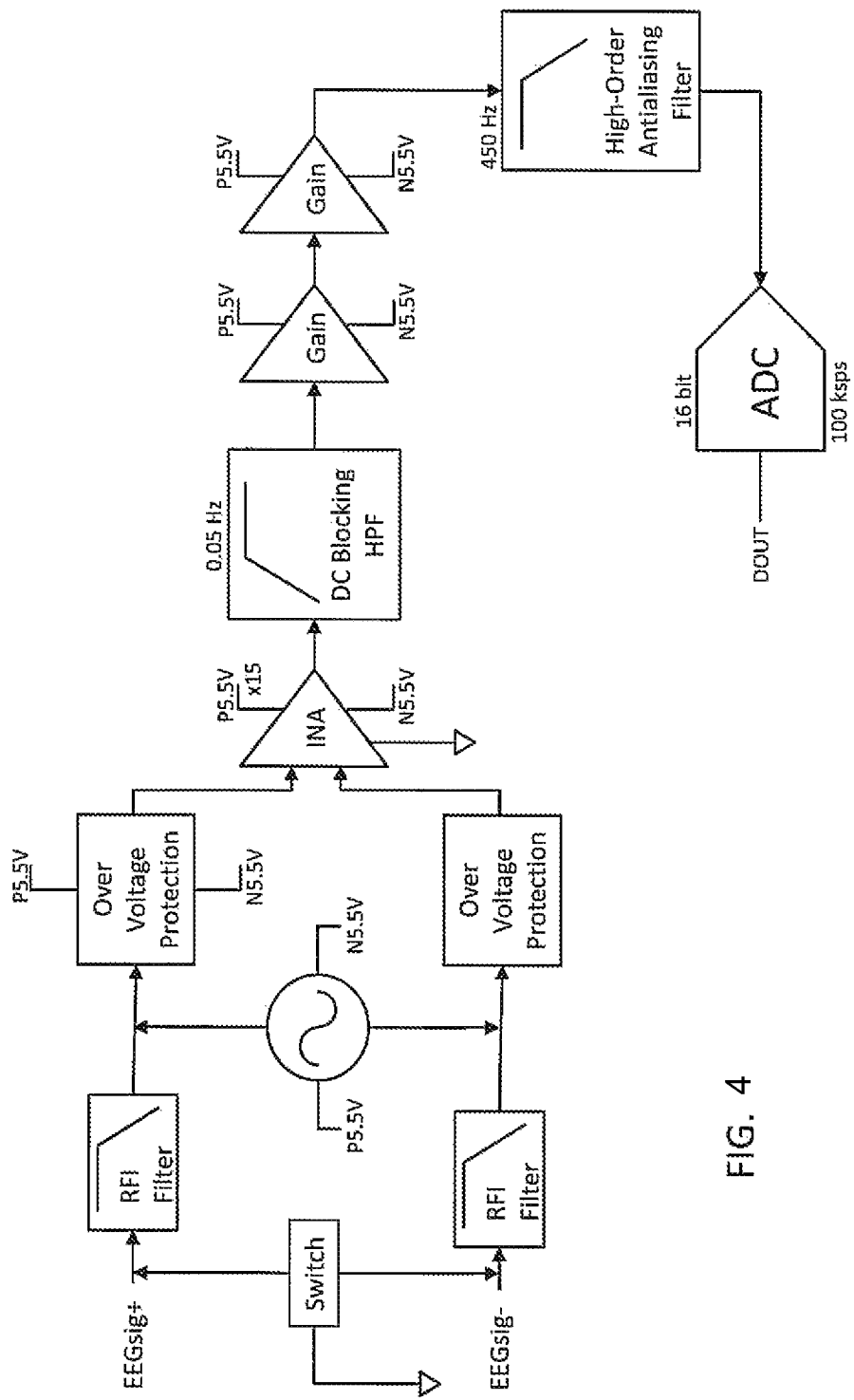
FIG. 4. Block diagram of an application-specific integrated circuit (ASIC) utilized in some embodiments of the device.

FIG. 4 is a block diagram of an application-specific integrated circuit (ASIC) used in certain embodiments of the present invention. The ASIC includes all the signal pre-processing function normally performed by a full-scale processor including amplification of the EEG signal, filtering of the signal, and analog-to-digital conversion. Preferably, the ASIC is constructed to be very small, substantially on the order of 0.2 square inches. Preferably, each channel of the physiological signal monitor has its own dedicated ASIC. This means that each channel has its own analog-to-digital converter, helping to minimize cross-talk between channels in the event that one or more channels should become disconnected during use. Separate amplification for each channel also minimizes amplifier noise, which leads to higher signal-to-noise and common-mode rejection ratios. More importantly, the ASIC chips consume extremely low power in comparison to general-purpose ICs, thus allowing the device to require lower power overall, permitting the device to require a smaller, lighter battery and helping to make the device lighter, longer-lasting, more portable, and disposable.

Figure 5:
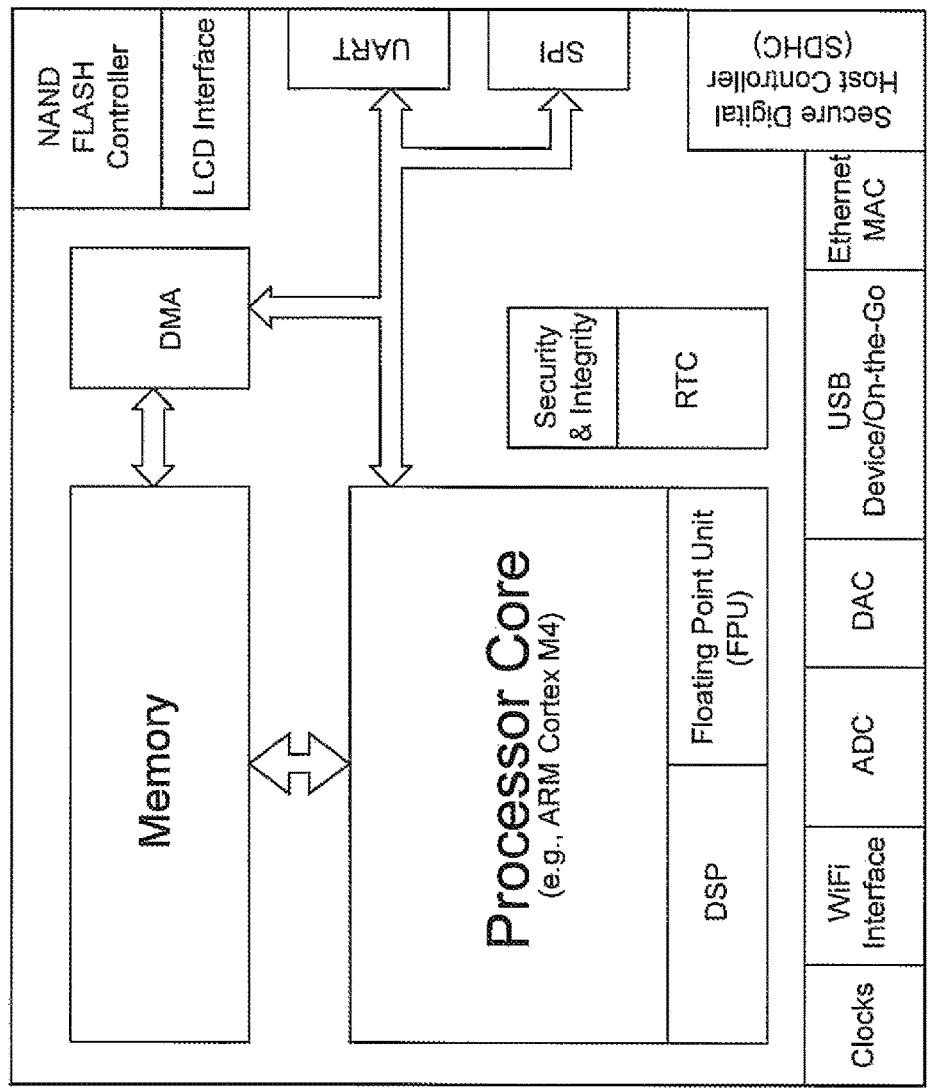
FIG. 5. System overview of one embodiment of the main processor for the physiological signal monitor.
Figure 6C:
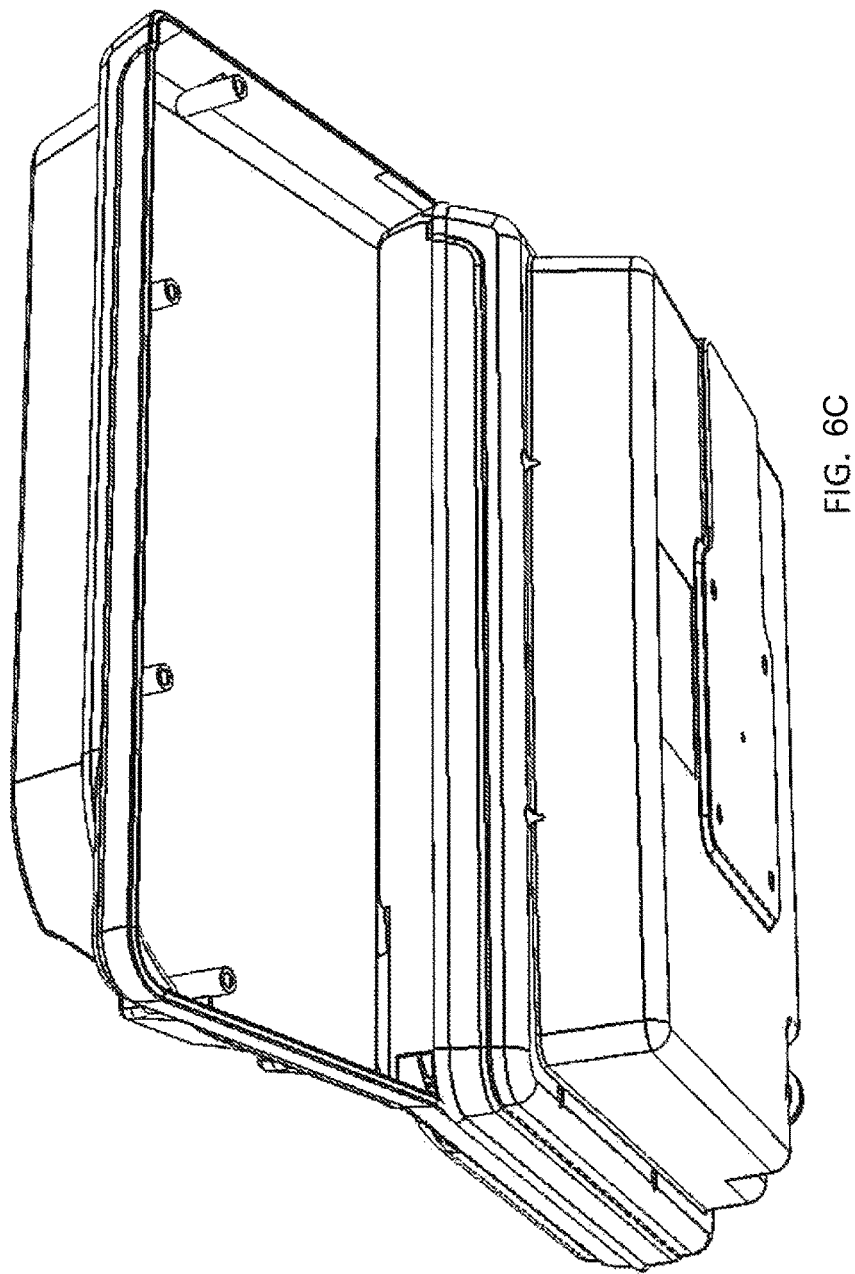
Figure 6D:
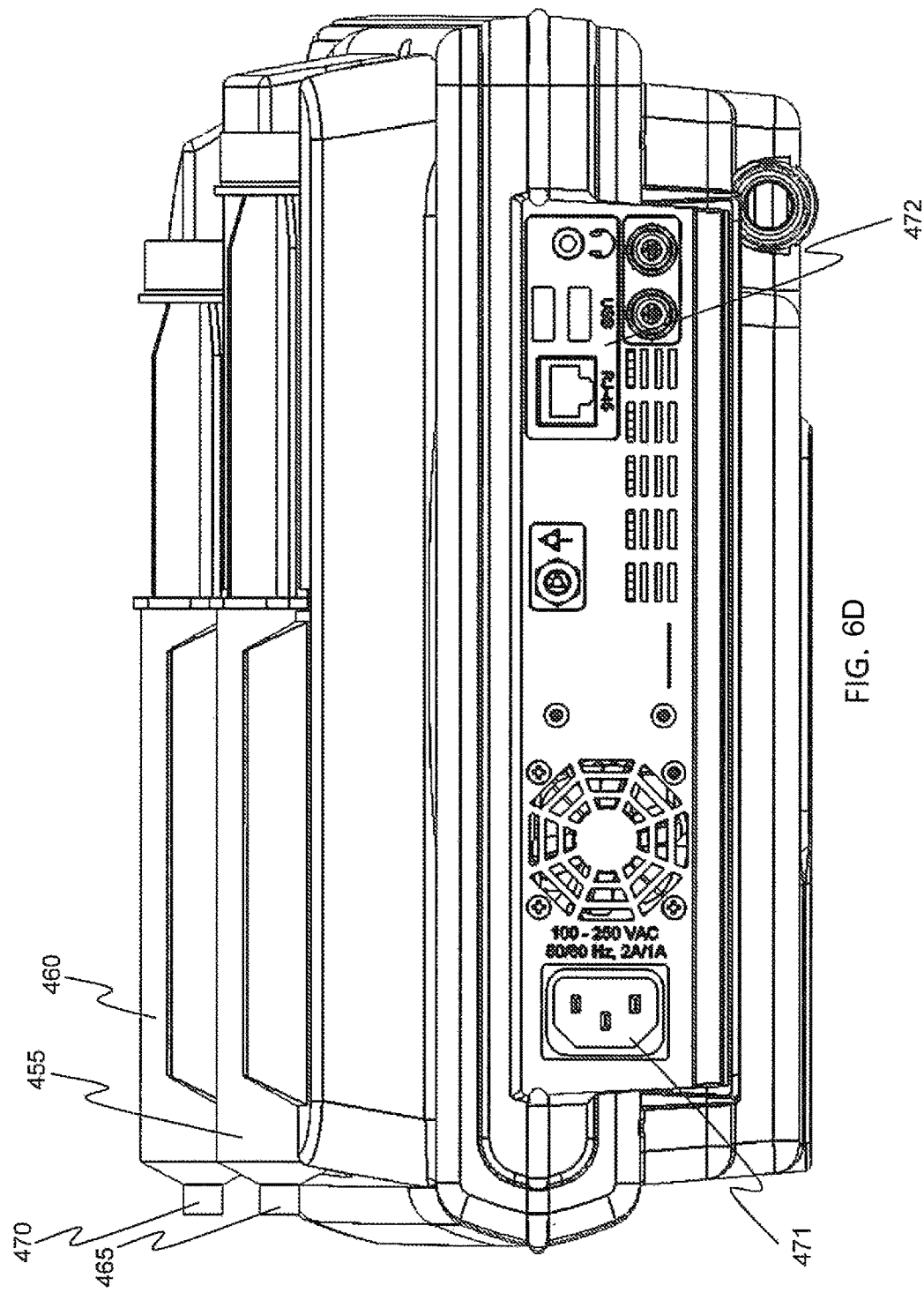
Figure 6H:
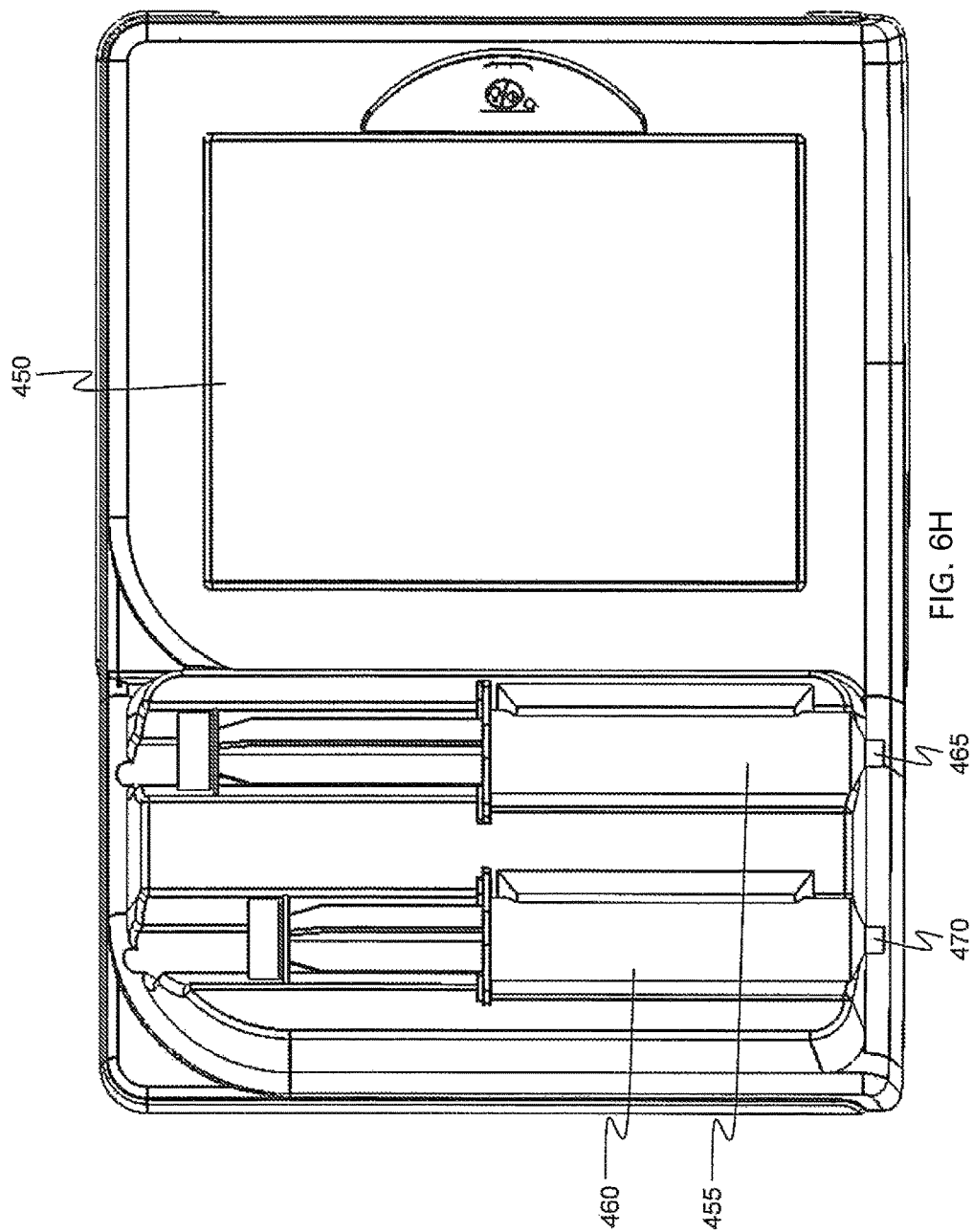
Figure 61:
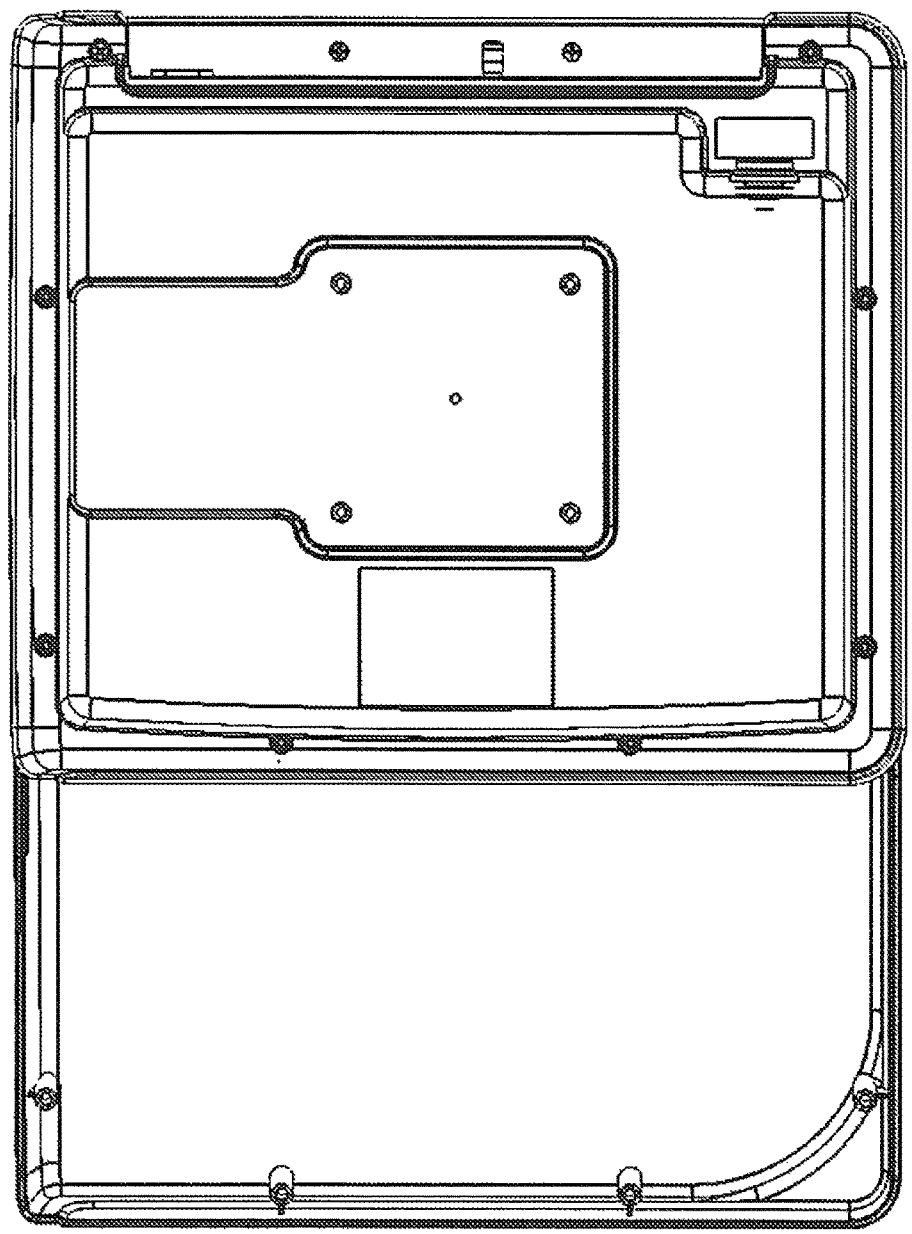

FIG. 5 is a list of features and components utilized in the physiological signal monitor's main processor. This processor is a micro-controller to help ensure the device is small, portable, and disposable, and was designed for mobile applications requiring small size and optimized power consumption. The processor is very low cost, and thus is easily integrated into a disposable product without significantly impacting the overall manufacturing costs. The exemplary depicted processor, an ARM Cortex-M4, provides all the necessary features required for processing a 4-channel EEG signal. First, the ARM processor embeds a powerful floating-point digital signal processor (DSP). This DSP is responsible for running in real-time all the processing algorithms including those for signal quality assessment, artifact detection and removal, seizure detection, cortical suppression detection and diminished consciousness detection.

The processor also features a 12-bit digital-to-analog converter (DAC), which can be used to generate the electrode impedance test signal. The present invention may preferably continuously perform impedance checking functions to verify the proper contact of the electrodes with the patient's skin. The impedance is measured by injecting a very small current at a predefined frequency, and measuring the voltage generated by this current across the electrodes. The frequency is typically outside the EEG bandwidth in order to avoid corruption of the signal of interest. The ARM DAC may be used to generate the sine waveform used to measure the electrode impedance.

Communication with the ASIC or IC chipsets may be carried out through a standard SPU/UART interface. The internal processor clock may sample each channel at 512 samples per second to guarantee a bandwidth up to 200 Hz. The ARM processor then outputs both the EEG and processed data onto its SPI bus or UART port.

FIGS. 6A through 6J illustrate different views of an embodiment of the IMIS device. The device comprises a display 450 and two syringe infusion pumps. The display 450 is used as a touchscreen user interface through which the user interacts with the device. Additionally, the display 450 is used to show any combination of indices, EEG signals, drug infusion rates, alerts or warnings, or any other information which may be useful or necessary to the user. The two syringe infusion pumps 455 and 460 are filled or attached to a drug source. Typically, at least one syringe infusion pump 455 is used to administer anesthetic or sedative medication. The second syringe infusion pump 460 may be an additional reservoir of anesthetic or sedative, or may be used to provide analgesic medication, or perhaps even muscle relaxation medication, or some other medication. Some embodiments may have more than two infusion pumps and thus provide any combination of these medications. The syringe infusion pumps 455 and 460 each have a line connection port 465 and 470, respectively, through which the medication is dispersed. A medical grade IV line is preferably used and connected to an IV inserted into the subject according to appropriate medical procedures. The drugs are pushed out of the syringe infusion pumps, through the line connection ports into the lines and thus into the subject.

The IMIS shown in FIGS. 6A through 6J may be powered by an internal battery (not illustrated), which may be replaceable or rechargeable, and/or by an external power source, and may be plugged in with any standard or special power connector. As illustrated, the IMIS has a standard IEC 60320 C14 AC power connector 471 and, internally, an AC-to-DC converter (not shown) allowing the IMIS to be plugged into a standard wall electrical outlet. Also, the IMIS embodiment illustrated has other connectors 472 such as RJ-45, USB, headphones, etc. for transfer of data and other signals to external sources. Additionally, the internal rechargeable battery of the IMIS may be recharged through any of the connectors 471, 472 which allow for transfer of electrical power, including the Ethernet port and the USB ports.

FIGS. 7A through 7H are screenshots of one embodiment of the display output of the IMIS system in use. The display is preferably a touchscreen interface which has integrated buttons, e.g., 520, 521, 522, by which the user can interact with the display. These touchscreen buttons allow the user to setup the device and begin its operation, change the display parameters, change the drug infusion rate, and otherwise interact with the device. In the upper left corner 500, the recorded EEG signals of each hemisphere are displayed individually. In the upper right corner 505, the $WAV_{CNS}$ index for each hemisphere is displayed individually, as well as the suppression ratio for each hemisphere. The lower left corner 510 shows a graph of the $WAV_{CNS}$ index for each hemisphere, but this corner may be programmed or adjusted to show other graphs, or multiple graphs at once, of different parameters, including $WAV_{CNS}$, suppression ratio, electromyography (EMG) activity in the signal, etc. The left-side portion has several touchscreen buttons which can be used to change the particular parameters which are displayed. The lower right side 515 displays the current volume of each drug (propofol and remifentanil in these particular screenshots) remaining in the device, or available to the system, as well as the rate of each drug's infusion. Each drug has its own window with control buttons thereby providing individual control for each drug. The user may also press the flag button 522 to insert flags 523 representative of important events or observations into the recorded data in real time. These flags can assist with later review of the data by marking such events or observations.

Figure 7A:
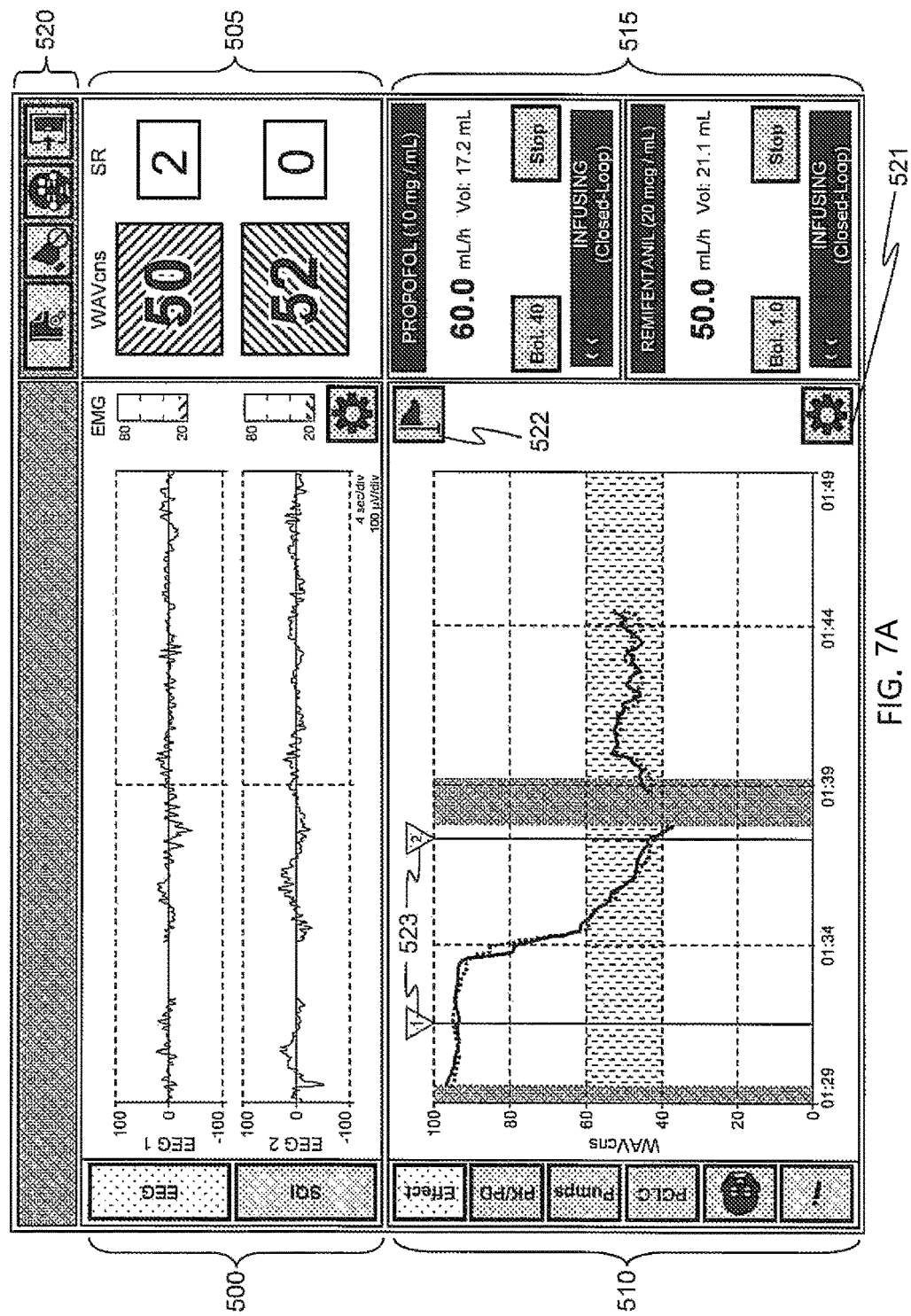
Figure 7B:
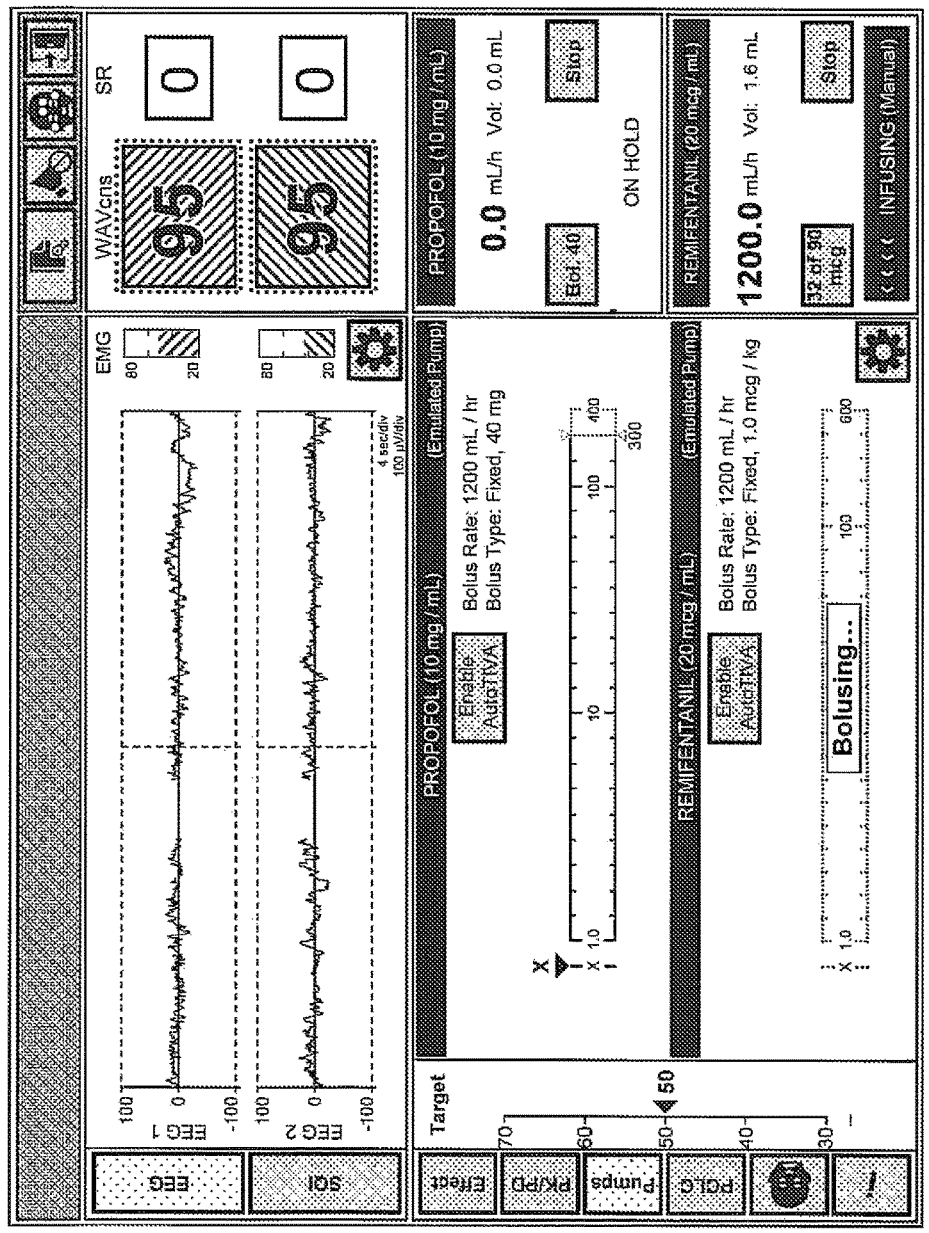
Figure 7C:
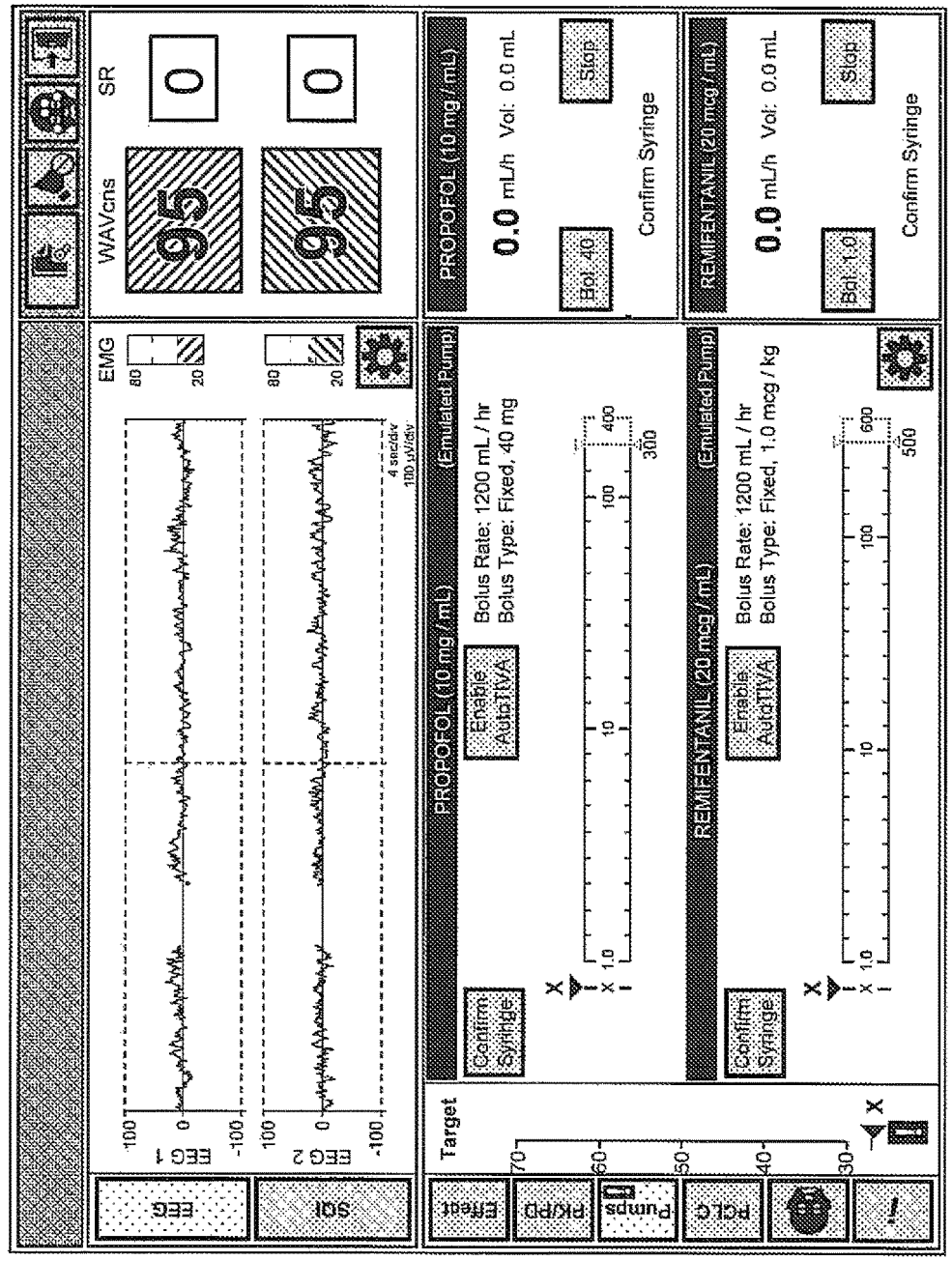

FIG. 7B shows how the drugs may be automatically infused by the system, or put on hold (propofol) or manually infused (remifentanil) in increments by the push of a button on the user interface.

Figure 7D:
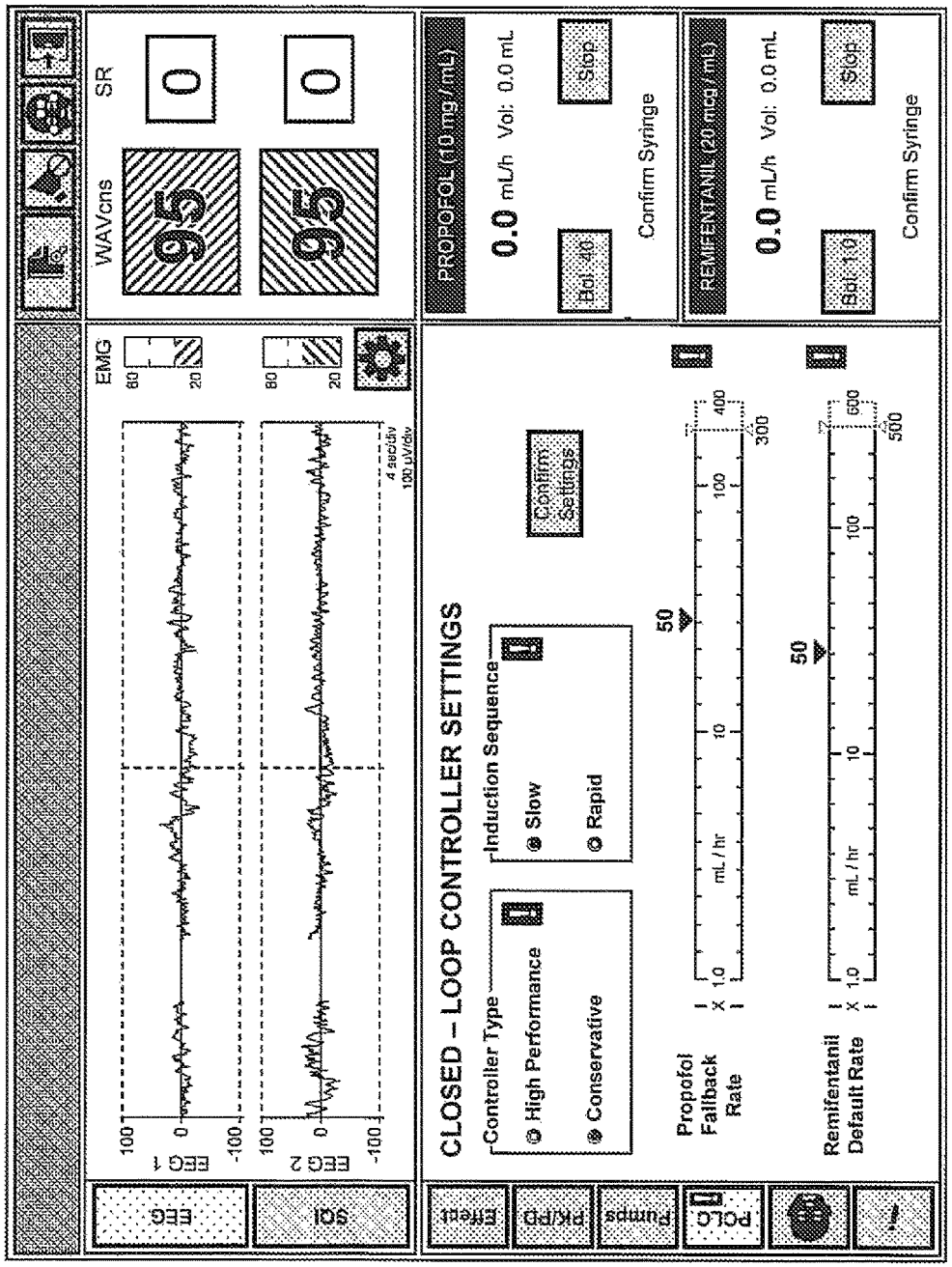
Figure 7E:
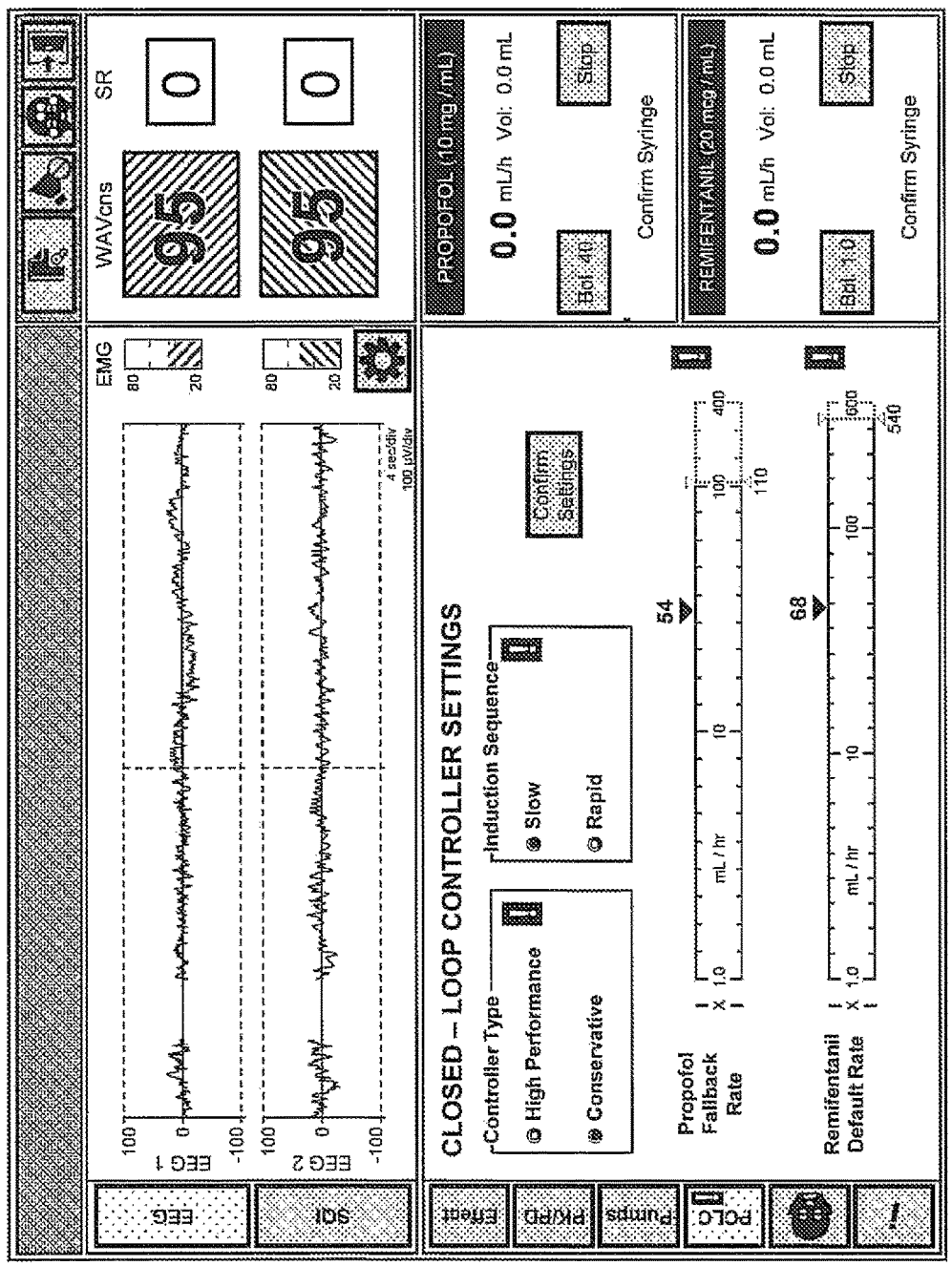
Figure 7F:
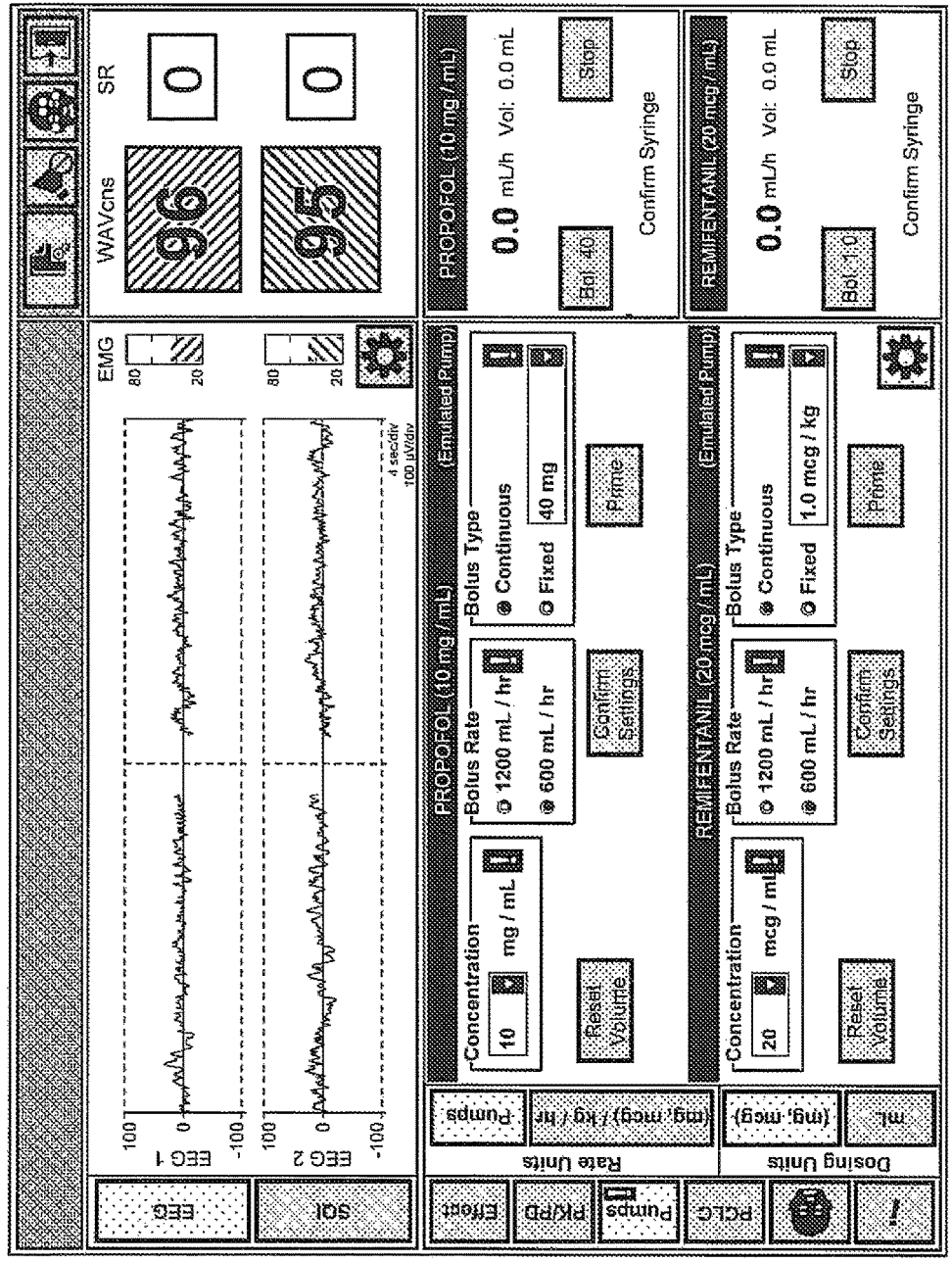
Figure 7G:
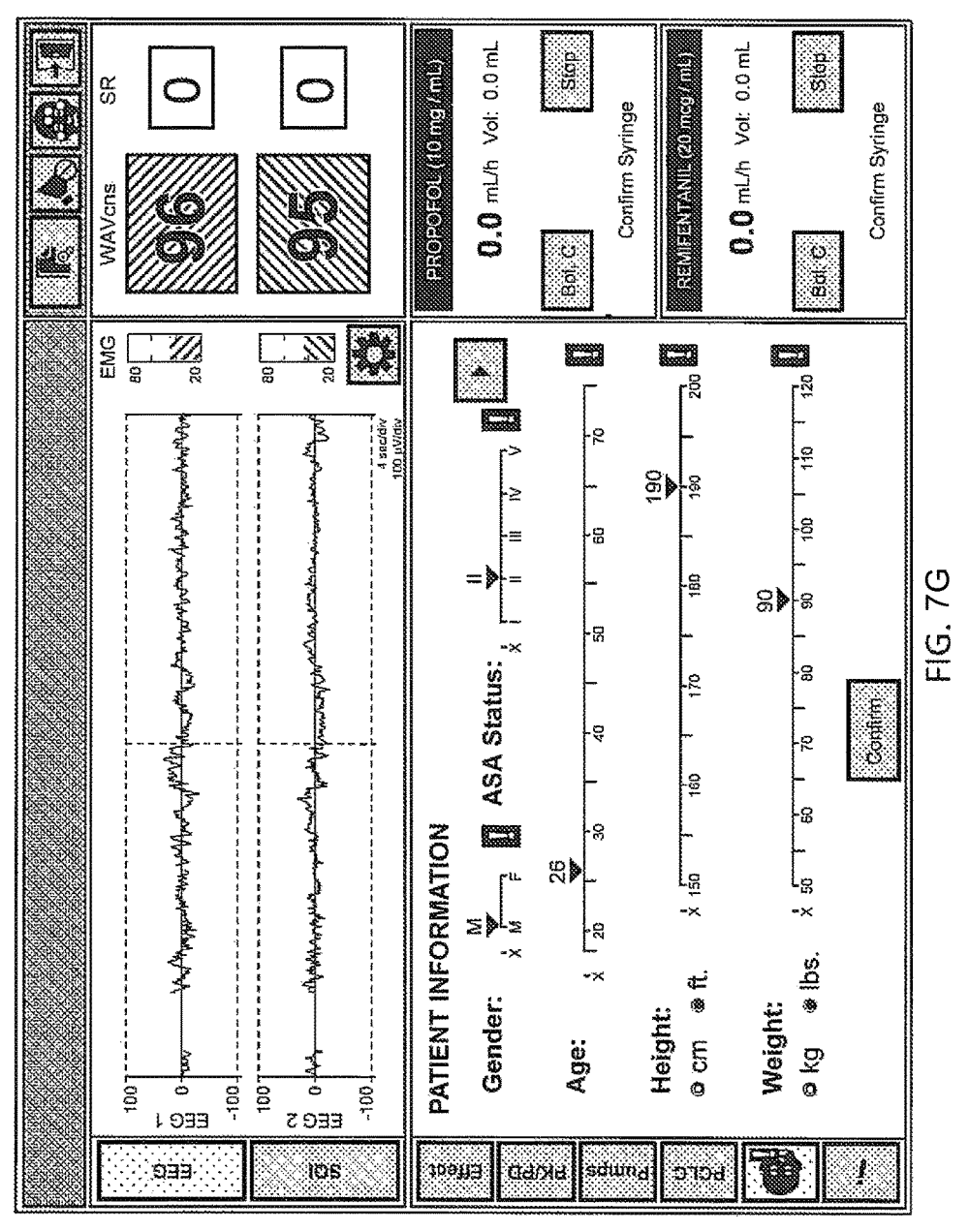
Figure 7H:
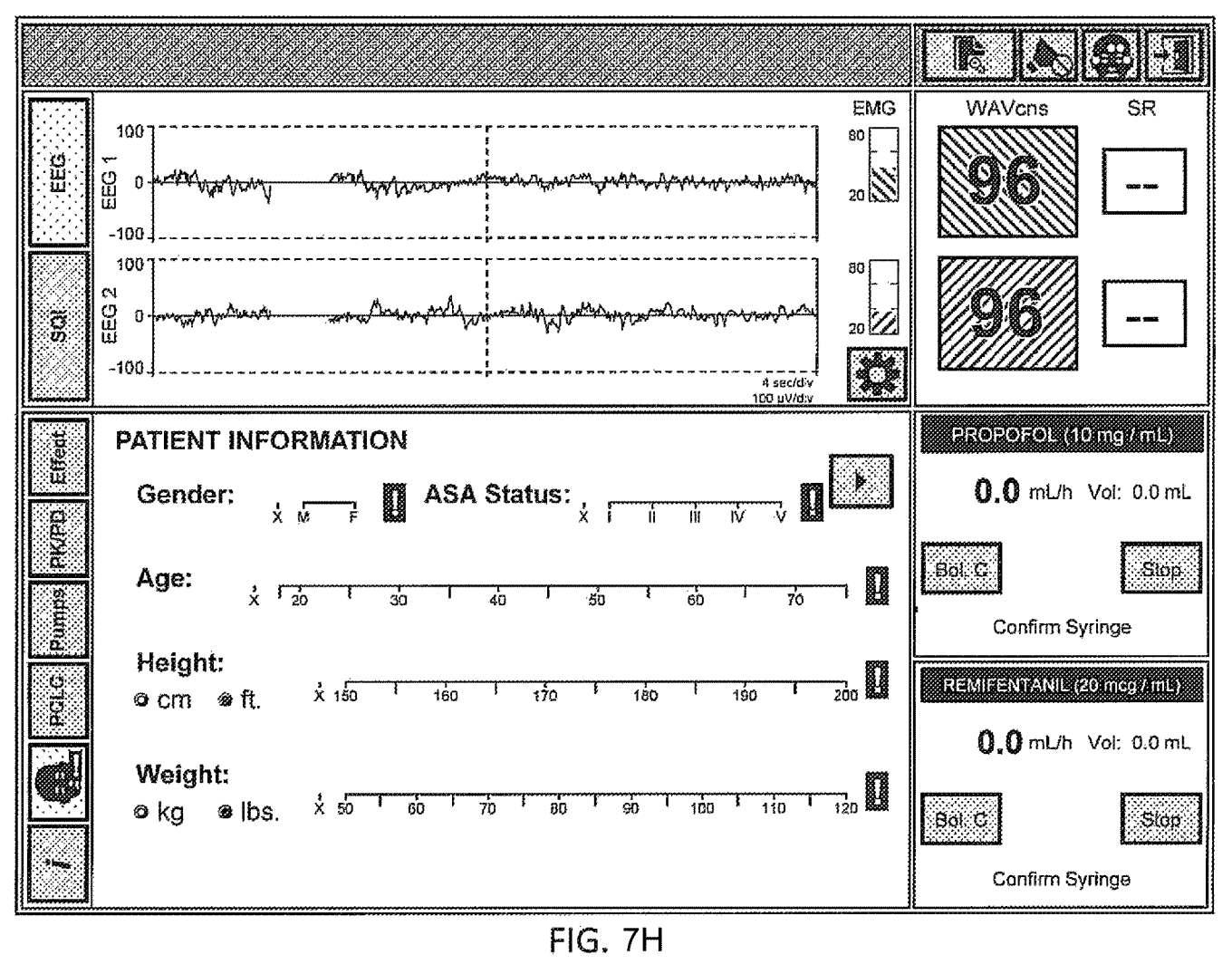

FIGS. 7D, 7E, and 7F show how closed-loop controller settings and drug settings must be entered and confirmed before closed-loop delivery of the drug(s) can begin. FIGS. 7G and 7H show how patient information settings must be entered and confirmed before closed-loop delivery of the drug(s) can begin. In the FIGS. 7C through 7F, "exclamation point" icons mark settings which must be confirmed, or which are otherwise detected as requiring adjustment, before drug delivery can commence.

FIG. 8 is an electrode/display integrated block diagram showing the arrangement of components in the physiological signal monitor and IMIS of some embodiments of the present invention. EEG signals are collected from an electrode array 1201 having a plurality of electrodes which are printed on, embedded in, etc., a full-flexible or semi-flexible substrate 1220 along with electronic components for RFI filtering and over-voltage protection 1202, amplifying, digitizing, and other signal acquisition tasks 1203, and controlling and/or processing the acquired data 1204. Together all these components form the electrode array 1220 discussed elsewhere in this application. Data from this electrode array is, in some embodiments, wired or wirelessly transmitted over a link 1205 to a monitor 1206 which may further process the data with a processor 1207, store raw and/or processed data in a memory 1208, and output raw and/or processed data to a display 1209. Embodiments that integrate the electrode array and the monitor into one disposable device are called by the term physiological signal monitor 1230 in this application.

Optionally, the same data link 1205 may be used to also send data from the electrode array 1220 and/or monitor 1206 to an integrated monitoring and infusion system (IMIS) 1210. Here, the raw or processed data is optionally further processed by CPU 1211 which comprises PID controller 1212 for output on a display 1213 and/or control of one or more infusion pumps 1217, 1218, 1219, etc. to deliver drugs to the patient or subject (not shown). The IMIS is controlled by a user interface 1214 which may include a keyboard, mouse, stylus, touchscreen, voice operation, or any other suitable interface. Signals, processed data and/or dosage logs are stored on a memory 1215. Audio feedback, including alarms that indicate dosages and/or patient status such as detected patient consciousness/alertness, or occurrence of burst suppression for example, may be provided by speaker 1216. As discussed previously, the pumps may be syringe pumps, peristaltic pumps, volumetric pumps, gravity-based pumps, or any other type of pump recognized as preferred for the particular application.

Together, the physiological signal monitor and IMIS systems form an automated closed-loop sedation or anesthesia system capable of being applied by a person with minimal training, and requiring no continuous human interaction or continuous human presence at the bedside. Preferably, the physiological signal monitor of the present invention provides that all equipment and functionality of the system is placed directly on the forehead of the patient or subject. The physiological signal monitor provides at least three EEG electrodes, and preferably at least six EEG electrodes. Preferably, the physiological signal monitor provides at least two channels of EEG, and more preferably at least four channels.

Figure 9:
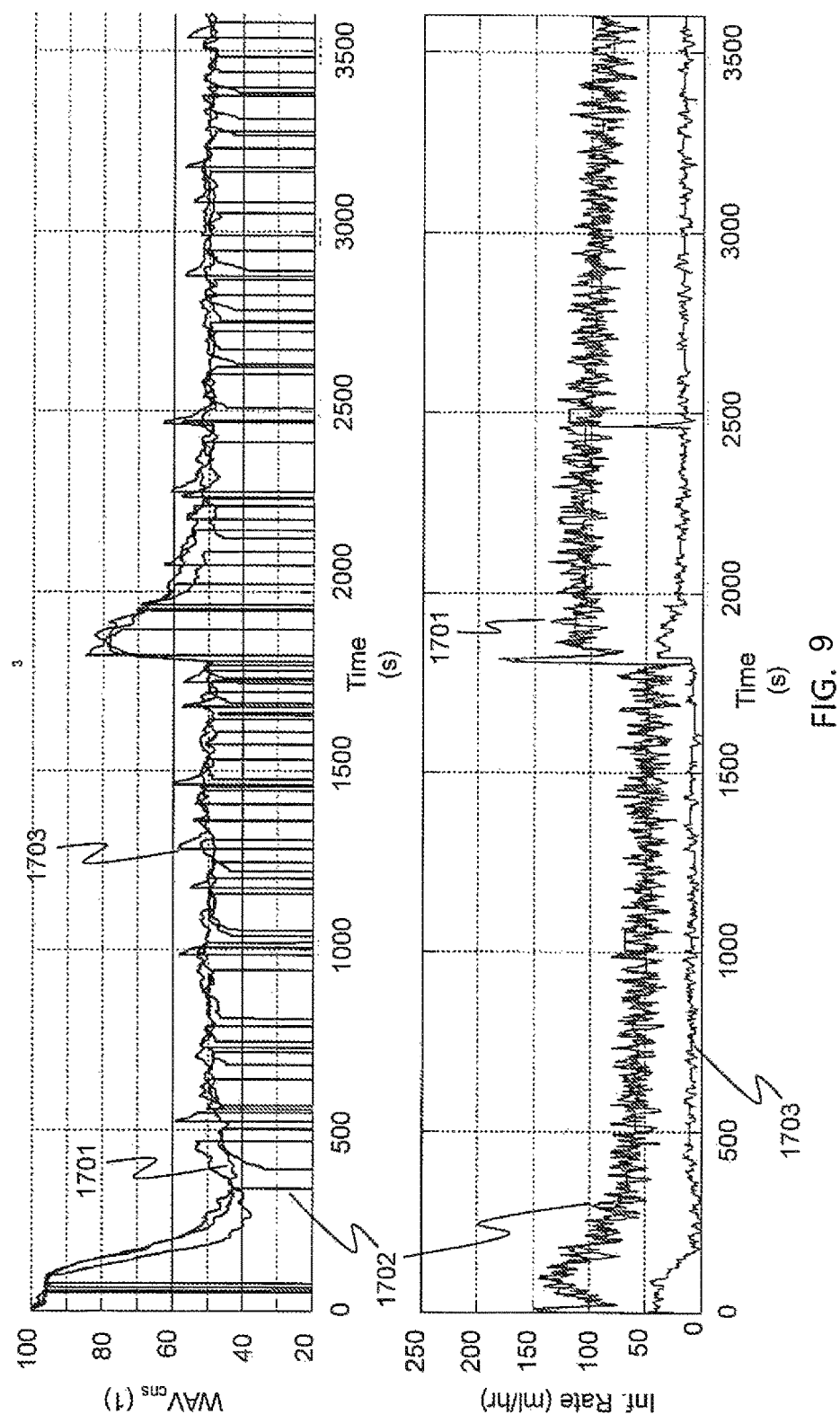
FIG. 9. Robust Predictive and Sparse controller: during gaps in the feedback variable, different robust predictive PID controllers with longer refreshing rates are used. In this example, WAVCNS data gaps are represented with vertical lines.

FIG. 9 presents the results of a simulated case of a control scheme that takes care of 99% of all feedback variable gaps. Gaps longer than 60 seconds trigger the default infusion rate set by the user at the start of the case (the default rate the user selected in case closed-loop operation must be discontinued). In the example case whose results are depicted in the present figure, a target of data gaps less than 50 seconds was set and the system was set to induce the patient. At t=1800 seconds, a large +30 unit disturbance is simulated, corresponding to a surgical stimulation. Line 1701 corresponds to the ideal situation where there is no data gap. Line 1702 simulates the effect of data gaps of random duration and randomly distributed in the case. As can be seen in this example, the sparse robust predictive PID controller succeeds in maintaining a high level of performance despite the feedback signal loss. FIG. 9 also shows the simulated result for the same patient while in severe hypovolemic shock (line 1703—note how the overall Propofol infusion rate is much lower).

(Note: the data gaps being random, the simulation line 1702 and the simulation line 1703 do not have the gaps at the same location.)

Figure 10A:
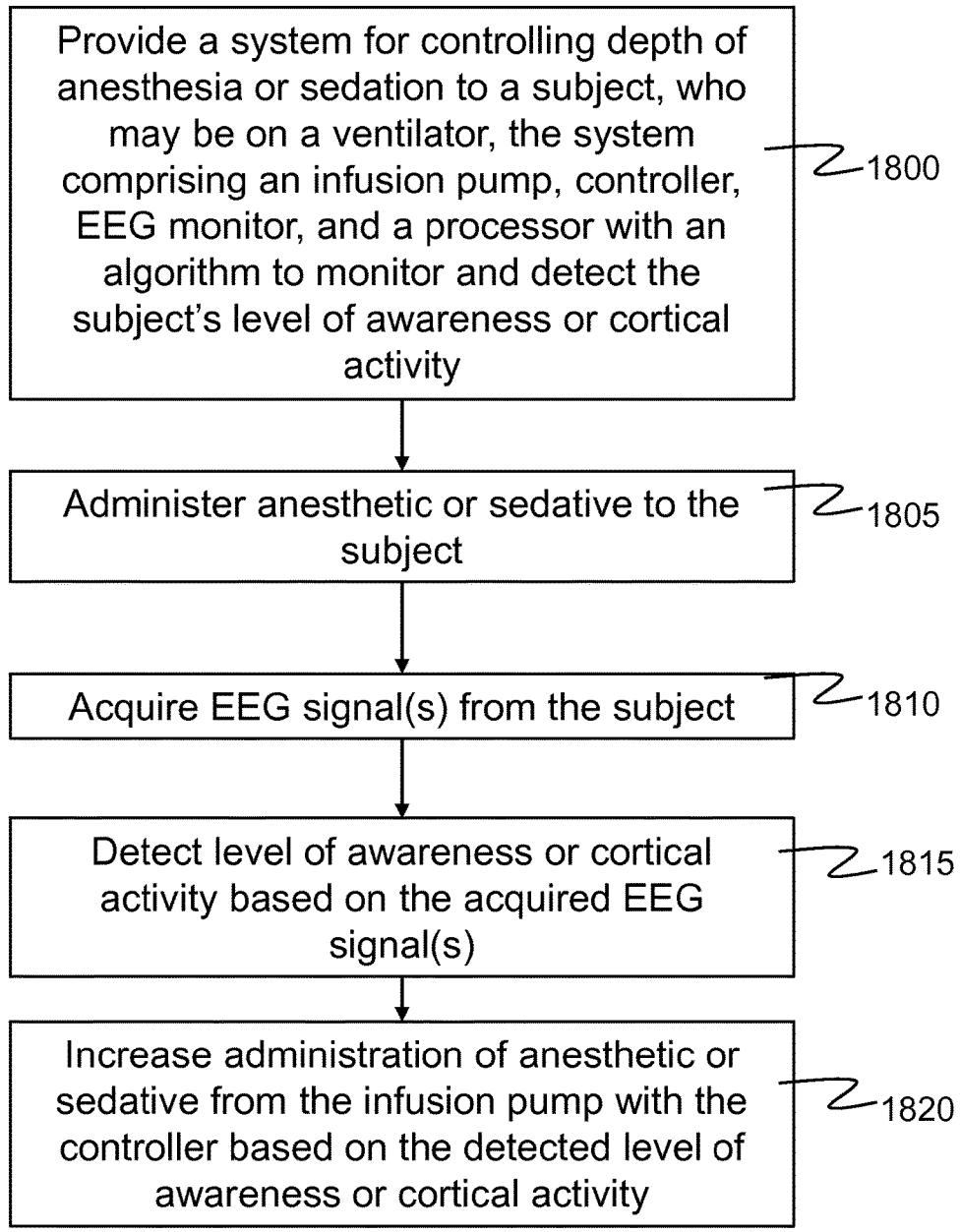
FIGS. 10A-10B. Flow charts depicting steps of various method embodiments of the present invention for monitoring and detecting a subject's level of awareness or cortical activity and controlling the level of anesthesia or sedation to ensure the subject maintains a sufficient level of anesthesia or sedation.
Figure 10B:
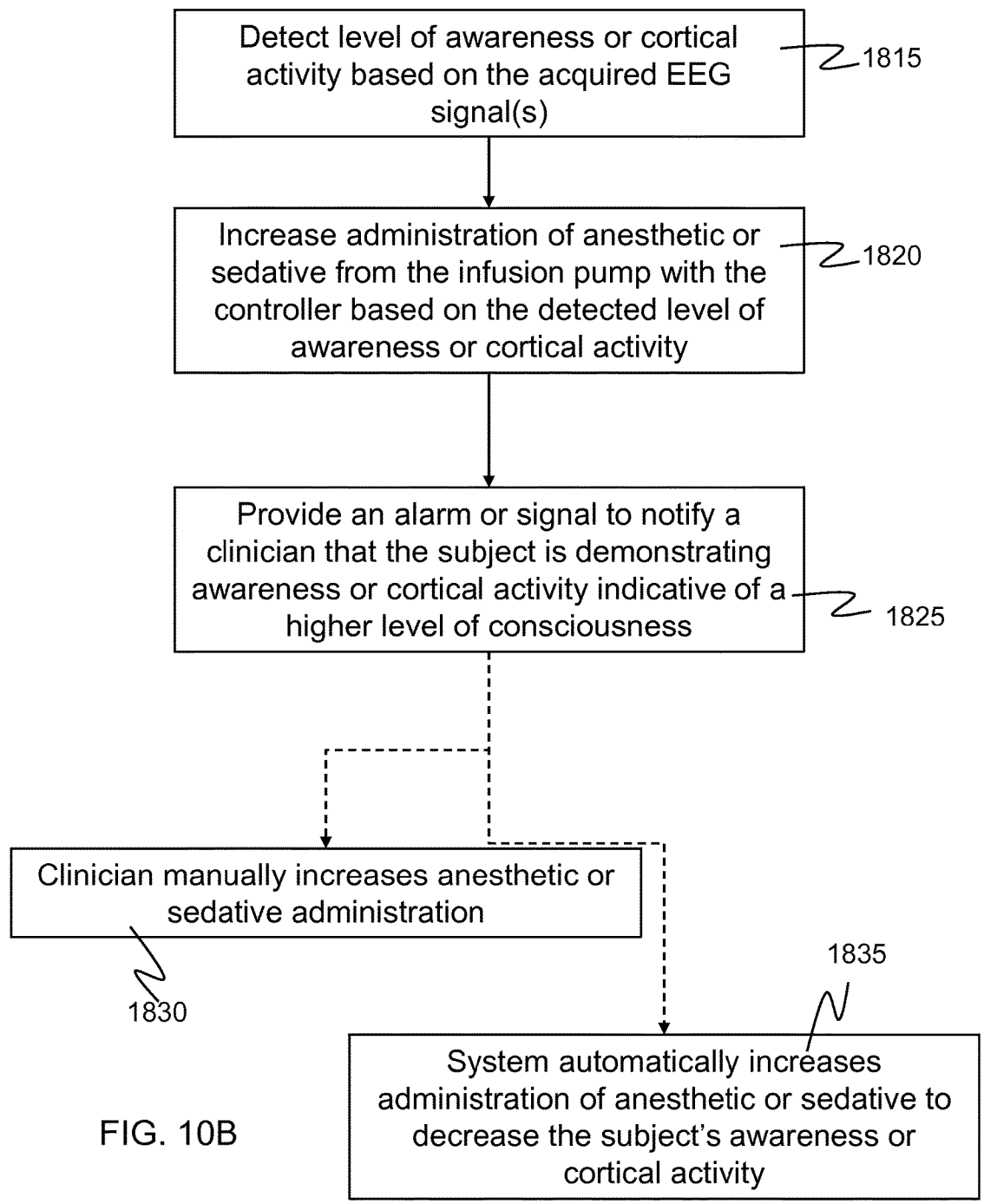

FIGS. 10A and 10B depict two flow charts presenting potential steps involved in method embodiments of the present invention wherein FIG. 10A shows a general method for controlling a subject's depth of anesthesia or sedation and ensuring that the subject is sufficiently anesthetized or sedated so as to avoid consciousness or awareness and harm to the subject, and FIG. 10B shows additional or optional steps that may be included along with the general method or process. In FIG. 10A, the first step 1800 involves providing a system for controlling the subject's depth of anesthesia or sedation. Such system is preferably as described herein and may include any of the disclosed embodiments with any or all of the features. Preferably, the provided system comprises at least an infusion pump or pump(s) adapted to administer an anesthetic or sedative to the subject, a controller adapted to provide commands to and otherwise controlling operation of the infusion pump, a physiological signal monitor (such as an EEG monitor) adapted to acquire physiological signals from the subject, and a processor comprising an algorithm adapted to process and analyze the physiological signals and to monitor and detect the subject's level of awareness or cortical activity. Depending on the particular embodiment, the subject may be attached to or on a ventilator. Once such a system is provided, the next step is to administer, using the provided system, an anesthetic or sedative to the subject 1805. Another step is to acquire a physiological signal from the subject 1810. The physiological signal is preferably at least acquired while the subject is under anesthesia or sedation, but more preferably may be acquired prior to, during and after anesthesia or sedation, and preferably on a substantially continuous basis. As the physiological signal is acquired, the processor and algorithm substantially continuously analyze the signal, and monitor and detect the subject's level of awareness or cortical activity 1815 from the physiological signal. The level of awareness or cortical activity may preferably be in the form of a quantitative index, as described herein, which provides a clear indication on a known scale of the subject's level of awareness or cortical activity as compared to the anesthetic or sedative depth. Alternatively, the level of awareness may be a separate measurement or indicator that is based on the calculated index, and/or some other indicator or signal (such as a different physiological signal, e.g., EOG or EMG signal). When a level of awareness or cortical activity that is too high, indicative possible consciousness or awareness of the subject, is detected, the system then increases administration of the anesthetic or sedative from the infusion pump 1820 by sending a command from the controller based on the detected level of awareness or cortical activity. Thus, the method aims to control the subject's depth of anesthesia or sedation by trying to maintain a desired or predetermined level thereof, and not letting the subject either come out too early, or become too aware.

FIG. 10B again depicts the steps of monitoring and detecting a level of awareness or cortical activity 1815 and increasing administration of the anesthetic or sedative 1820, but further depicts additional or optional steps that may be included to further ensure the subject's safety while controlling the depth of anesthesia or sedation. One such additional or optional step would be to provide a signal or alarm via an output device adapted to notify a clinician that the subject's level of awareness or cortical activity is too high and/or that the subject requires clinician attention 1825. This alarm or signal serves to have a clinician come and tend to the subject to ensure that he or she is not coming out of anesthesia, and thus serves to minimize the harm or damage to the subject. If the subject's level of awareness or cortical activity is too high, there are several options for increasing the administration of anesthetic or sedative to achieve a desired depth of anesthesia or sedation: 1) the clinician may manually increase administration of the anesthetic or sedative 1830; or 2) the system can determine, either independently (closed-loop) or with clinician prompting (semi-closed-loop) to monitor the subject's physiological signal(s), that the subject's level of awareness or cortical activity is too high, and the system can then automatically increase administration of the anesthesia or sedation 1835.

Figure 11A:
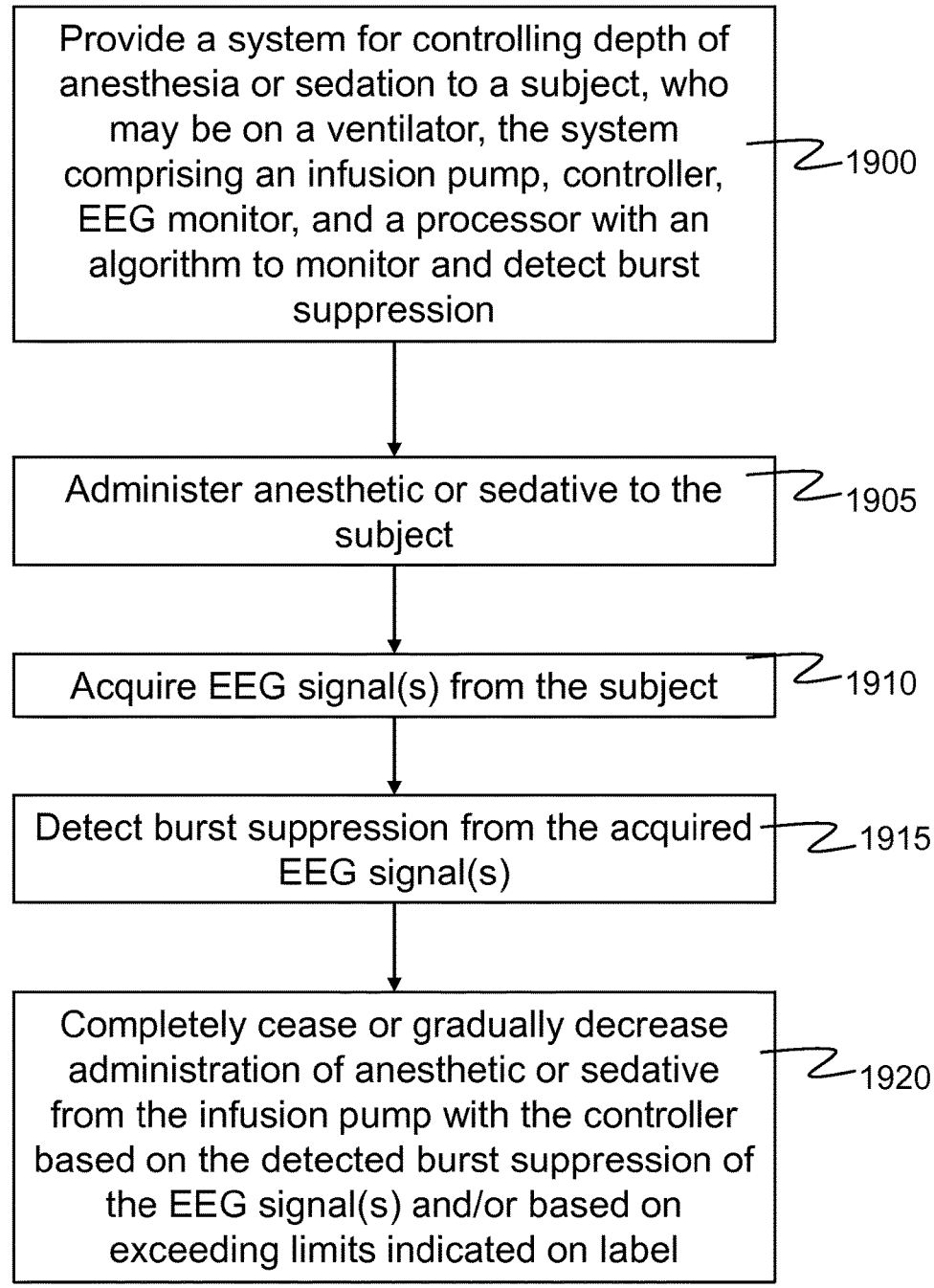
FIGS. 11A-11B. Flow charts depicting steps of various method embodiments of the present invention for monitoring and detecting a subject's level of anesthesia or sedation and determining the occurrence of an unsafe depth of anesthesia or sedation and controlling said level to ensure the subject maintains a sufficient level of anesthesia or sedation.
Figure 11B:
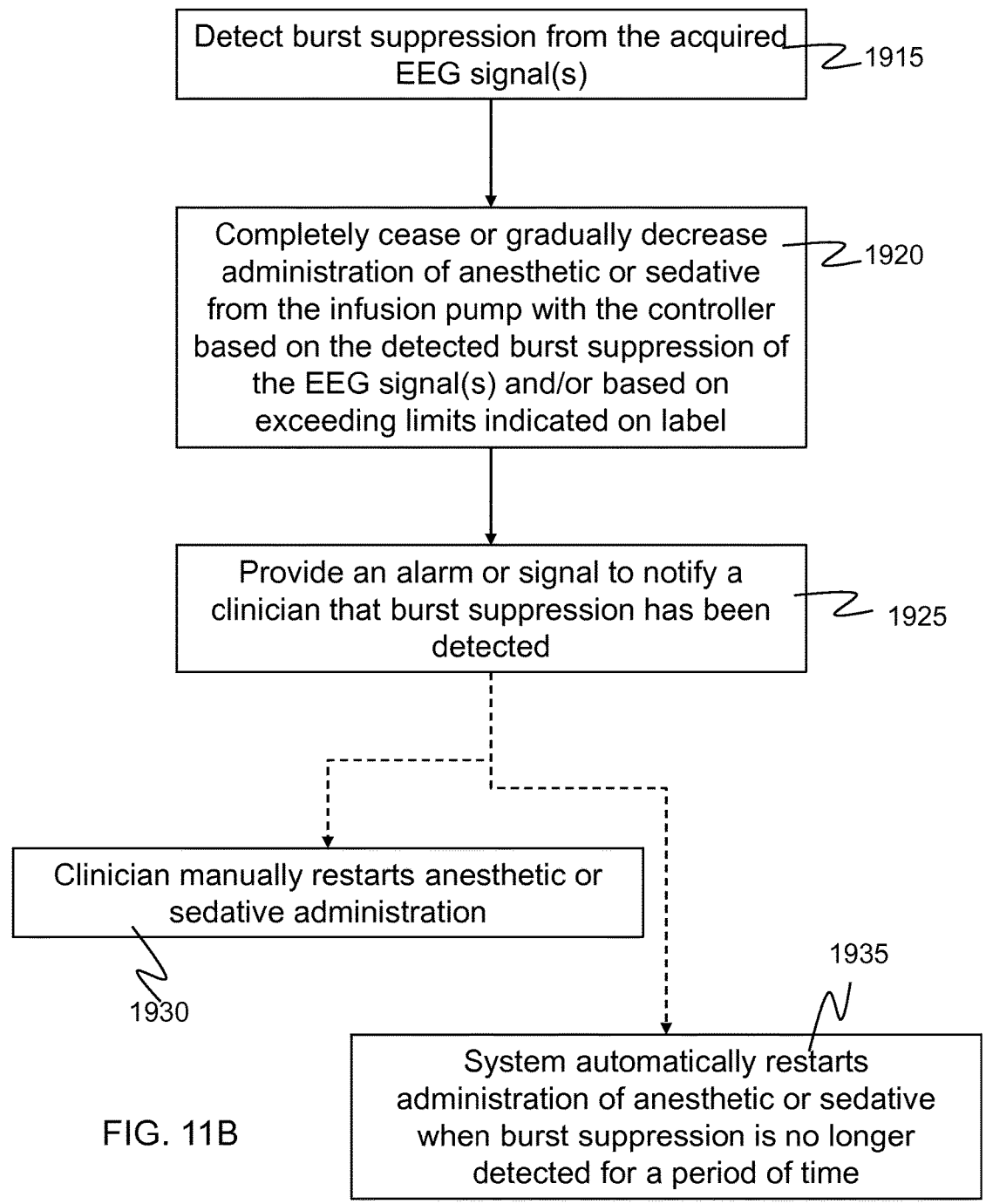

FIGS. 11A and 11B depict two flow charts presenting potential steps involved in method embodiments of the present invention wherein FIG. 11A shows a general method for controlling a subject's depth of anesthesia or sedation and FIG. 11B shows additional or optional steps that may be included along with the general method or process. In FIG. 11A, the first step 1900 involves providing a system for controlling the subject's depth of anesthesia or sedation. Such system is preferably as described herein and may include any of the disclosed embodiments with any or all of the features. Preferably, the provided system comprises at least an infusion pump or pump(s) adapted to administer an anesthetic or sedative to the subject, a controller adapted to provide commands to and otherwise controlling operation of the infusion pump, a physiological signal monitor (such as an EEG monitor) adapted to acquire physiological signals from the subject, and a processor comprising an algorithm adapted to process and analyze the physiological signals and to detect abnormal or unsafe conditions of the subject based on the acquired physiological signal, one specific example of such a condition being burst suppression. Depending on the particular embodiment, the subject may be attached to or on a ventilator. Once such a system is provided, the next step is to administer, using the provided system, an anesthetic or sedative to the subject 1905. Another step is to acquire a physiological signal from the subject 1910. The physiological signal is preferably at least acquired while the subject is under anesthesia or sedation, but more preferably may be acquired prior to, during and after anesthesia or sedation, and preferably on a substantially continuous basis. As the physiological signal is acquired, the processor and algorithm substantially continuously analyze the signal, and may detect the occurrence of an abnormal or unsafe condition, such as burst suppression 1915 from the physiological signal. When such condition is detected, the system then ceases or decreases administration of the anesthetic or sedative from the infusion pump 1920 by sending a command from the controller based on the detected abnormal or unsafe condition. Thus, the method aims to control the subject's depth of anesthesia or sedation by trying to maintain a desired or predetermined level thereof, and not letting the subject go too deep.

FIG. 11B again depicts the steps of detecting an abnormal or unsafe condition, such as burst suppression, of the physiological signal 1915 and ceasing or decreasing administration of the anesthetic or sedative 1920, but further depicts additional or optional steps that may be included to further ensure the subject's safety while controlling the depth of anesthesia or sedation. One such additional or optional step would be to provide a signal or alarm via an output device adapted to notify a clinician that an abnormal or unsafe condition has been detected and/or that the subject requires clinician attention 1920. This alarm or signal serves to have a clinician come and tend to the subject to ensure that he or she is neither coming out of anesthesia or sedation nor going to deep, and thus serves to minimize the harm or damage to the subject. Once the subject is determined to be in a safe condition, there are several options for resuming operation of the system to continue providing anesthetic or sedative: 1) the clinician may manually resume or restart operation of the system 1930; or 2) the system can determine, either independently (closed-loop) or with clinician prompting (semi-closed-loop) to monitor the subject's physiological signal(s), that the abnormal or unsafe condition is no longer occurring and/or has not occurred for a predetermined amount of time, and can then automatically increase or resume administration of the anesthesia or sedation 1935.

While a preferred embodiment is disclosed herein, it will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A system for controlling anesthesia or sedation of a subject, the system comprising:
    a physiological signal sensor adapted to acquire a physiological signal from a subject indicative of the subject's electroencephalogram (EEG) signal;
    an infusion pump adapted to administer anesthetic or sedative to the subject; and
    a controller adapted to control the infusion pump and administration of the anesthetic or sedative; the controller comprising a processor adapted for receiving the physiological signal from the physiological signal sensor and further comprising an algorithm adapted to perform real-time quantitative monitoring of the physiological signal and from this monitoring to detect burst suppression of the subject's EEG signal from the physiological signal,
    wherein the controller is further adapted to stop anesthetic or sedative administration via the infusion pump based upon a level of burst suppression of the subject's EEG signal.

2. The system of claim 1, wherein the algorithm is adapted to calculate a numerical index representative of a level of cortical activity or depth of anesthesia or sedation of the subject using a wavelet analysis of the EEG signal, and the controller is adapted to control the administration of anesthetic or sedative in order to keep the numerical index at a desired or predetermined level corresponding to a desired or predetermined level of consciousness.

3. The system of claim 1, further comprising an output device adapted to provide an alarm or signal to a clinician, the alarm or signal adapted to notify the clinician when the burst suppression of the EEG signal has been detected and the administration of the anesthetic or sedative has been stopped.

4. The system of claim 3, wherein the controller is adapted such that the clinician must reset or instruct the system to be able to resume administration of anesthetic or sedative to the subject.

5. The system of claim 3, wherein the controller is adapted such that the system automatically resumes administration of anesthetic or sedative when the burst suppression of the EEG signal is not detected for a predetermined period of time.

6. The system of claim 3, wherein the controller is programmed to administer the anesthetic or sedative according to label indications of the particular anesthetic or sedative being delivered such that the system cannot exceed recommended dosage unless a clinician programs the controller to do so.

7. The system of claim 6, wherein the controller is adapted such that the system additionally ceases administration of the anesthetic or sedative with the infusion pump when the administered anesthetic or sedative reaches at least one limit programmed according to the label indications of the anesthetic or sedative.

8. A system for controlling anesthesia or sedation of a subject, the system comprising:
    a physiological signal sensor adapted to acquire a physiological signal from a subject indicative of the subject's electroencephalogram (EEG) signal;
    an infusion pump adapted to administer anesthetic or sedative to the subject; and
    a controller adapted to control the infusion pump and administration of the anesthetic or sedative; the controller comprising a processor adapted for receiving the physiological signal from the physiological signal sensor and further comprising an algorithm adapted to perform real-time quantitative monitoring of the physiological signal and from this monitoring to detect burst suppression of the subject's EEG signal from the physiological signal,
    wherein the controller calculates a numerical index representative of a level of cortical activity or depth of anesthesia or sedation of the subject, and the controller is adapted to control the administration of anesthetic or sedative in order to maintain the numerical index at a desired or predetermined level corresponding to a desired or predetermined level of consciousness, and further to reduce or stop anesthetic or sedative administration below that being used to maintain the desired or predetermined numerical index level via the infusion pump based upon a level of burst suppression of the subject's EEG signal.

9. The system of claim 8, wherein the algorithm is adapted to calculate the numerical index representative of a level of cortical activity or depth of anesthesia or sedation of the subject using a wavelet analysis of the EEG signal.

10. The system of claim 8, further comprising an output device adapted to provide an alarm to a clinician, the alarm adapted to notify the clinician that the burst suppression of the EEG signal has been detected.

11. The system of claim 10, wherein the controller is adapted such that the clinician must reset or instruct the system to be able to increase or resume administration of anesthetic or sedative to the subject.

12. The system of claim 10, wherein the controller is adapted such that the system automatically increases or resumes administration of anesthetic or sedative when the burst suppression of the EEG signal is not detected for a predetermined period of time.

13. The system of claim 10, wherein the controller is programmed to administer the anesthetic or sedative according to label indications of the particular anesthetic or sedative being delivered such that the system cannot exceed recommended dosage unless a clinician programs the controller to do so.

14. The system of claim 13, wherein the controller is adapted such that the system additionally ceases administration of the anesthetic or sedative with the infusion pump when the administered anesthetic or sedative reaches at least one limit programmed according to the label indications of the anesthetic or sedative.

15. A system for controlling sedation of a subject, the system comprising:

a physiological signal sensor adapted to acquire a physiological signal from a subject indicative of the subject's electroencephalogram (EEG) signal;

an infusion pump adapted to administer anesthetic or sedative to the subject; and a controller adapted to control the infusion pump and administration of the anesthetic or sedative; the controller comprising a processor adapted for receiving the physiological signal from the physiological signal sensor and further comprising an algorithm adapted to perform real-time quantitative monitoring of the physiological signal and from this monitoring to detect burst suppression of the subject's EEG signal from the physiological signal, wherein the controller is further adapted to reduce or stop the anesthetic or sedative administration via the infusion pump based upon a level of burst suppression of the subject's EEG signal.

16. The system of claim 15, wherein the algorithm is adapted to calculate a numerical index representative of a level of cortical activity or depth of anesthesia or sedation of the subject using a wavelet analysis of the EEG signal.

17. The system of claim 15, further comprising an output device adapted to provide an alarm to a clinician, the alarm adapted to notify the clinician that the burst suppression of the EEG signal has been detected.

18. The system of claim 17, wherein the controller is adapted such that the clinician must reset or instruct the system to be able to increase or resume administration of the anesthetic or sedative to the subject.

19. The system of claim 17, wherein the controller is adapted such that the system automatically increases or resumes administration of the anesthetic or sedative when the burst suppression of the EEG signal is not detected for a predetermined period of time.

20. The system of claim 17, wherein the controller is programmed to administer the anesthetic or sedative according to label indications of the particular anesthetic or sedative being delivered such that the system cannot exceed recommended dosage unless a clinician programs the controller to do so.

* * * * *